(12) United States Patent
Yoshida et al.

(10) Patent No.: US 7,147,843 B2
(45) Date of Patent: Dec. 12, 2006

(54) HAIR GROOMING PREPARATION

(75) Inventors: Katsunori Yoshida, Yokohama (JP); Takahiro Akutsu, Yokohama (JP); Katsuo Hashimoto, Yokohama (JP); Isamu Kaneda, Yokohama (JP); Toshio Yanaki, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 10/049,110

(22) PCT Filed: Jun. 26, 2001

(86) PCT No.: PCT/JP01/05438

§ 371 (c)(1),
(2), (4) Date: Feb. 8, 2002

(87) PCT Pub. No.: WO02/00179

PCT Pub. Date: Jan. 3, 2002

(65) Prior Publication Data

US 2003/0012761 A1    Jan. 16, 2003

(30) Foreign Application Priority Data

Jun. 26, 2000  (JP)  ............................. 2000-190944
Jun. 26, 2000  (JP)  ............................. 2000-190946

(51) Int. Cl.
*A61Q 5/02*  (2006.01)
*A61Q 5/00*  (2006.01)

(52) U.S. Cl. ..................................... 424/70.9; 424/70.1

(58) Field of Classification Search ................ 424/401, 424/70.1, 70.12, 70.11, 70.22; 514/772, 514/772.3
See application file for complete search history.

(56) References Cited

U.S. PATENT DOCUMENTS 6,174,522 B1 * 1/2001 Baravetto et al. ......... 424/70.12
6,365,142 B1 * 4/2002 Tamura .................... 424/70.17

FOREIGN PATENT DOCUMENTS

EP     0 978 522 A    2/2000
WO     WO 99/40891 A  8/1999

* cited by examiner

*Primary Examiner*—Jyothsna Venkat
(74) *Attorney, Agent, or Firm*—Townsend & Banta

(57) ABSTRACT

A hair treatment agent composition characteristically comprising a specific hydrophobically modified polyether urethane and cationic surfactant.

The hair treatment agent composition of the present invention provides has good temperature stability in terms of the viscosity, exhibits superior fluid flow characteristics, achieves smoothness and ease of arranging the hair after drying, and gives a superior sensation during use.

A cleaning agent composition characteristically comprising a specific hydrophobically modified polyether urethane and anionic surfactant and/or ampholytic surfactant.

The cleaning agent composition of the present invention has superior viscosity and is superior in terms of foam formation as well as foam durability and feels refreshing without a slimy sensation after rinsing-off.

6 Claims, No Drawings

HAIR GROOMING PREPARATION

TECHNICAL FIELD

The present invention relates to a hair treatment agent composition. More particularly, it relates to a hair treatment agent composition which has superior temperature stability of the viscosity and superior sensation during use; it relates especially to a hair conditioning agent.

The present invention relates to a cleaning agent composition. More particularly, the present invention relates to a cleaning agent composition that has superior viscosity and is superior in foam formation and foam durability, and feels refreshing without a slimy sensation after rinsing-off.

BACKGROUND ART

Hair treatment agent compositions having so-called conditioning effects which endow hair with smoothness and gloss and make combing easier are commonly sold in the markets under names such as "hair rinse", "hair treatment", "hair conditioner", and "hair pack".

A quartenary ammonium salt is blended in many of these hair treatment agent compositions as a main ingredient; it is adsorbed onto hair to give the aforementioned conditioning effects, which is a publicly known fact.

A practice of blending in a higher alcohol to form a gel-like complex with the quarternary ammonium salt and even adding liquid oils, waxes, silicone compounds, and natural and synthetic polymers as necessary is also publicly known.

However, when conventional hair treatment agent compositions are used, while smoothness and such can be given to the hair without causing stickiness at the time of application and during rinsing, satisfactory smoothness and ease of arranging the hair are hard to come by at the time of towel drying after rinsing, during hair drying, and after drying.

Also, since many of the aforementioned hair conditioning agents use a complex of a quarternary ammonium salt and a higher alcohol for the conditioning ingredient, the viscosity of the prepared product is determined by the contents and blend ratios of these, which puts many restrictions on recipes; adjusting the viscosity to the desired level while also adjusting the sensation during use is very difficult.

In addition, the aforementioned complex of the quarternary ammonium salt and the higher alcohol varies in its structure, i.e. lamella-vesicle, depending on the preparation method; this makes it difficult to adjust the viscosity to a fixed level; not only that, the temperature dependence of the viscosity of a hair conditioning agent containing such a complex is closely related to the melting point of the complex and, specifically, a steep reduction in the viscosity is observed at temperatures near the melting point, which is accompanied by a steep reduction in the stability of the product.

On the other hand, if, for purposes of solving the aforementioned problems, a thickener, such as a so-called polymer thickener commonly used in cosmetics including carboxyvinyl polymer and xanthan gum, is blended in these hair treatment agent compositions then various troubles arise. For example, since many of these polymer thickeners are anionic polymer electrolytes, they form a complex with the cationic surfactant contained in the hair conditioner and cause precipitation, which is not desirable for the stability and appearance of the product. Also, if a polymer thickener other than the anionic ones is blended in, an undesirable sensation during use occurs after rinsing-off, such as sliminess, which is characteristic of polymers.

Recently, a sensitive engineering method has been adopted for evaluating product characteristics during makeup application, and various factors have been found to be related to consumers' taste for the products. Particularly regarding hair conditioning agents, various investigations have been conducted to improve the tactile sensation during rinsing, after towel drying, and after drying; the aforementioned new investigation method has revealed that consumers pay significant attention to the tactile sensation when putting the product on their hands and to the experience of applying and spreading it on their hair. In such a process, adjusting the fluid flow characteristics (rheological characteristics) of the product to the consumers' liking becomes important. For this purpose, a hair treatment agent composition with proper viscosity and fluid flow characteristics is desired.

In view of the aforementioned problem, the inventors conducted earnest research and discovered that a composition comprising a cationic surfactant and hydrophobically modified polyether urethane which can associate in a water sobluble medium to increase the viscosity of the water soluble medium can solve the aforementioned problems and exhibits superior performance as a hair treatment agent composition, thus completing the present invention.

The object of the present invention is to provide a hair treatment agent composition which has good temperature stability in terms of viscosity, exhibits superior fluid flow characteristics, achieves smoothness and ease of arranging the hair after drying, and gives a superior sensation during use.

In the field of cleaning agents, many products are found in the market in the form of, for example, hair shampoo, body shampoo, face washing agents, etc. which have had their viscosity adjusted for ease of handling by adding a suitable thickener to a surfactant solution.

Usually, a few percent to a few tens of percent of a surfactant, mainly an anionic surfactant solution, is blended into these products for the purpose of adequate foaming and stain removal; in order to thicken a highly concentrated anionic surfactant solution, typically an ampholytic surfactant, cationic surfactant, and/or lipophilic nonionic surfactant, and/or the addition of a salt such as sodium chloride is combined in to promote micelle growth and thicken the system.

However, some anionic surfactants, such as N-acylmethyl taurate, N-acyl taurate, N-acyl isethionate, fatty acid soaps, and amino acid type surfactants, do not grow micelles easily even with addition of the aforementioned additives; as a result, giving sufficiently satisfactory viscosity to the product is difficult.

When the desired viscosity cannot be obtained, problems such as dripping occur during use; not only that, the feel during the use of the product, which recent consumers regard as very important, including sensory characteristics such as a rich sensation from adequate viscosity and ease of spreading, is difficult to satisfy, and therefore it is very difficult to receive high appreciation in the market.

On the other hand, if a thickener, such as a so-called polymer thickener commonly used in cosmetics including carboxyvinyl polymer and xanthan gum, is blended in these cleaning agent compositions then various troubles arise. For example, when these polymer thickeners are blended in, foaming, which is regarded as the most important characteristic of a cleaning agent, is hindered; furthermore, the foam once formed becomes easy to break, resulting in problems in the durability of foam and such. Also, if a polymer thickener is used, an undesirable sensation during use occurs after rinsing-off, such as sliminess, which is characteristic of polymers. Furthermore, in a highly concentrated surfactant solution, the surfactant acts as a kind of salt and the solubility of the polymer is reduced due to salting out. In such cases, not only is the polymer thickener's effect not exhibited but also the product has a fatal problem such as precipitation of the thickener over time.

In view of the aforementioned problem, the inventors conducted earnest research to discover that a composition comprising an anionic surfactant or ampholytic surfactant and hydrophobically modified polyether urethane which can associate in a water sobluble medium to increase the viscosity of the water soluble medium can solve the aforementioned problems and exhibits superior performance as a cleaning agent, thus completing the present invention.

The object of the present invention is to provide a cleaning agent composition that has superior viscosity and is superior in foam formation and foam durability, and feels refreshing without a slimy sensation after rinsing-off.

DISCLOSURE OF INVENTION

That is, the present invention provides a hair treatment agent characteristically comprising the following ingredients (A) and (B):
(A) Hydrophobically modified polyether urethane represented by the following general formula (1):

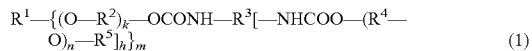

[In this formula, $R^1$, $R^2$, and $R^4$ denote hydrocarbon groups which can be identical or different from each other; $R^3$ denotes a hydrocarbon group that can have a urethane bond; $R^5$ denotes a straight chain, branched chain, or secondary hydrocarbon group (having 24 or more, preferably 24, carbon atoms); m is the number 2 or greater; h is the number 1 or greater; and k and n are independent numbers in the range of 0–1,000.]
(B) Cationic surfactant Also, the present invention provides the aforementioned hair treatment agent composition wherein $R^2$ and/or $R^4$ in general formula (1) for the hydrophobically modified polyether urethane are alkylene groups having 2–4 carbon atoms or phenylethylene groups that can be identical or different from each other.

Furthermore, the present invention provides the aforementioned hair treatment agent composition wherein $R^3$ in general formula (1) for the hydrophobically modified polyether urethane is a polyisocyanate residue represented by $R^3$—$(NCO)_{h+1}$.

Also, the present invention provides said cleaning agent composition wherein said polyisocyanate residue represented by $R^3$—$(NCO)_{h+1}$ is a polyisocyanate residue obtained by a reaction between di- to octa- hydric polyol and di- to tetra-hydric polyisocyanate.

Furthermore, the present invention provides the aforementioned hair treatment agent composition wherein $R^1$ in general formula (1) for the hydrophobically modified polyether urethane is a polyol represented by $R^1$—$(OH)_m$.

Furthermore, the present invention provides the aforementioned hair treatment agent composition wherein $R^5$ in general formula (1) for the hydrophobically modified polyether urethane is a hydrocarbon group derived from decyltetradecyl alcohol.

Furthermore, the present invention provides the aforementioned hair treatment agent composition wherein the hydrophobically modified polyether urethane represented by general formula (1) is a product of a reaction between one, two or more polyether polyols represented by $R^1$—$[(O-R^2)_k-OH]_m$, one, two or more polyisocyanates represented by $R^3$—$(NCO)_{h+1}$, and one, two or more polyether monoalcohols represented by $HO-(R^4-O)_n-R^5$.

Furthermore, the present invention provides the aforementioned hair treatment agent composition wherein the cationic surfactant is a quarternary ammonium salt represented by the following general formula (2) or an amidoamine type compound represented by the following general formula (3).

[In this formula, R3 denotes an alkyl group or hydroxyalkyl group having 14–22 carbon atoms, R4 denotes a benzyl group, hydroxyalkyl group, or alkyl group having 1–3 carbon atoms, R5 and R6 denote alkyl groups or hydroxyalkyl groups independently represented by either R3 or R4, and X denotes a halogen atom or an alkylsulfuric group having 1–2 carbon atoms.]

[In this formula, R7CO— denotes a higher fatty acid residue having 12–24 carbon atoms, R8 denotes an alkyl group having 1–4 carbon atoms, and x is an integer 2–4.]

Also, the present invention provides the aforementioned hair treatment agent composition wherein said quarternary ammonium salt is one, two or more selected from a group consisting of stearyltrimethyl ammonium chloride, cetyltrimethyl ammonium chloride, and behenyltrimethyl ammonium chloride.

Furthermore, the present invention provides the aforementioned hair treatment composition wherein said amidoamine-type compound is one, two or more selected from a group consisting of stearamidoethyl diethylamine, stearamidopropyl dimethylamine, and behenamidopropyl dimethylamine.

Also, the present invention provides the aforementioned hair treatment composition which additionally comprises a higher alcohol and/or higher fatty acid.

Furthermore, the present invention provides the aforementioned hair treatment agent composition wherein said higher alcohol is one, two or more selected from a group consisting of cetyl alcohol, stearyl alcohol, and behenyl alcohol.

Also, the present invention provides the aforementioned hair treatment agent composition, wherein said higher fatty acid is one, two or more selected from a group consisting of stearic acid, palmitic acid, myristic acid, oleic acid, isostearic acid, 12-hydroxystearic acid, or behenic acid.

Furthermore, the present invention provides the aforementioned hair treatment agent composition wherein the molar ratio of the cation surfactant and the higher alcohol and/or higher fatty acid is 1:2–1:10.

Also, the present invention provides the aforementioned hair treatment agent composition wherein the blend ratio of the hydrophobically modified polyether urethane of general formula (1) is 0.1–10 wt % of the total amount of the hair treatment agent composition.

Also, the present invention provides the aforementioned hair treatment agent composition wherein the blend ratio of a cationic surfactant is 0.01–10 wt % of the total amount of the hair treatment agent composition.

Furthermore, the present invention provides the aforementioned hair treatment agent composition wherein the viscosity of the hair treatment agent composition is 1–10 Pa·s when measured at 25° C. and $1s^{-1}$ and/or 0.1–1 Pa·s when measured at 25° C. and $100s^{-1}$.

Furthermore, the present invention provides the aforementioned hair treatment agent composition wherein said hair treatment agent composition is a hair conditioning agent.

Furthermore, the present invention provides the aforementioned hair treatment agent composition which additionally contains organic acid (preferably tartaric acid or glutamic acid).

That is, the present invention provides a cleaning agent characteristically comprising the following ingredients (A) and (B):

(A) Hydrophobically modified polyether urethane represented by the following general formula (1):

General Formula (1)

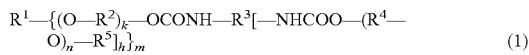

[In this formula, $R^1$, $R^2$, and $R^4$ denote hydrocarbon groups which can be identical or different from each other; $R^3$ denotes a hydrocarbon group that can have a urethane bond; $R^5$ denotes a straight chain, branched chain, or secondary hydrocarbon group (having 24 or more, preferably 24, carbon atoms); m is the number 2 or greater; h is the number 1 or greater; and k and n are independent numbers in the range of 0–1,000.]

(B) Anionic surfactant and/or ampholytic surfactant

Also, the present invention provides said cleaning agent composition wherein $R^2$ and/or $R^4$ in general formula (1) for the hydrophobically modified polyether urethane are alkylene groups having 2–4 carbon atoms or phenylethylene groups that can be identical or different from each other.

Furthermore, the present invention provides said cleaning agent composition wherein $R^3$ in general formula (1) for the hydrophobically modified polyether urethane is a polyisocyanate residue represented by $R^3$—$(NCO)_{h+1}$.

Also, the present invention provides said cleaning agent composition wherein said polyisocyanate residue represented by $R^3$—$(NCO)_{h+1}$ is a polyisocyanate residue obtained by a reaction between di- to octa- hydric polyol and di- to tetra-hydric polyisocyanate.

Furthermore, the present invention provides said cleaning agent composition wherein $R^1$ in general formula (1) for the hydrophobically modified polyether urethane is a polyol represented by $R^1$—$(OH)_m$.

Furthermore, the present invention provides said cleaning agent composition wherein $R^5$ in general formula (1) for the hydrophobically modified polyether urethane is a hydrocarbon group derived from decyltetradecyl alcohol.

Furthermore, the present invention provides said cleaning agent composition wherein the hydrophobically modified polyether urethane represented by general formula (1) is a product of a reaction between one, two or more polyether polyols represented by $R^1$—$[(O-R^2)_k-OH]_m$, one, two or more polyisocyanates represented by $R^3$—$(NCO)_{h+1}$, and one, two or more polyether monoalcohols represented by $HO$—$(R^4-O)_n$—$R^5$.

Also, the present invention provides said cleaning agent composition wherein the anionic surfactant is represented by the following general formulas (4), (5), or (6).

General Formula (4)

(In this formula, R1CO— denotes a saturated or unsaturated fatty acid residue having 10–22 carbon atoms on average; a denotes any of the structures containing electron donor atoms —O—, —NH—, and/or —N(CH$_3$)—; M1 denotes hydrogen, alkali metal, alkaline earth metal, ammonium or organic amine; and n denotes an integer 1–3.)

General Formula (5)

(In this formula, R2CO— denotes a saturated or unsaturated fatty acid residue having 10–22 carbon atoms on average; b denotes a hydrogen atom, —CH$_3$, or —(CH$_2$)n-COOM3; M2 and M3 denote hydrogen, alkali metal, alkaline earth metal, ammonium or organic amine; and n denotes an integer 1–3.)

General Formula (6)

(In this formula, R3COO— denotes a saturated or unsaturated fatty acid residue having 10–22 carbon atoms on average; M4 denotes hydrogen, alkali metal, alkaline earth metal, ammonium or organic amine; and n denotes an integer 1–3.)

Furthermore, the present invention provides said cleaning agent composition wherein the anionic surfactant is one, two, or more chosen from a group consisting of N-acylmethyl taurate, N-acyl taurate, and N-acyl isethionate.

Also, the present invention provides said cleaning agent composition wherein the ampholytic surfactant is an acetic acid betaine type or imidazoline type ampholytic surfactant.

Furthermore, the present invention provides said cleaning agent composition wherein the weight ratio between the anionic surfactant and the ampholytic surfactant is 10:0–2:8.

Also, the present invention provides said cleaning agent composition wherein the blend ratio of the hydrophobically modified polyether urethane of general formula (1) is 0.1–10 wt % of the total amount of the cleaning agent composition.

Furthermore, the present invention provides said cleaning agent composition wherein the blend ratio of the anionic surfactant or the ampholytic surfactant is 5–40 wt % of the total amount of the cleaning agent composition.

Also, the present invention provides the aforementioned cleaning agent composition wherein the viscosity of the cleaning agent composition is 1–10 Pa·s when measured at 25° C. and $1s^{-1}$ and/or 0.1–1 Pa·s when measured at 25° C. and $100s^{-1}$.

Furthermore, the present invention provides said cleaning agent composition which additionally contains cationized starch.

BEST MODE FOR CARRYING OUT THE INVENTION

The configuration of the present invention is described in detail below.

(A) Hydrophobically modified polyether polyurethane of general formula (1)

The hair treatment agent composition of the present invention contains a specific hydrophobic polyether polyurethane. The hydrophobically modified polyether polyurethane used in the present invention functions as an associative thickener and is capable of increasing the viscosity of a water soluble medium, and therefore is used as a viscosity adjusting agent (refer to Japanese Patent Laid-Open No. Hei 9-71766 bulletin, for example).

The hydrophobic polyether polyurethane represented by general formula (1) can be obtained by, for example, reacting one, two or more polyetherpolyols represented by $R^1$—$[(O—R^2)_k—OH]_m$, one, two or more polyisocyanates represented by $R^3$—$(NCO)_{h+1}$, and one, two or more polymonoalcohols represented by HO—$(R^4—O)_n$—$R^5$. In this case $R^1$–$R^5$ in general formula (1) is determined by the $R^1$—$[(O—R^2)_k—OH]_m$, $R^3$—$(NCO)_{h+1}$, and HO—$(R^4—O)$ n-$R^5$ used. The loading ratios of the three are not limited in particular; in terms of the ratio between the hydoxide group from the polyether polyol and the polyether monoalcohol and the isocyanate group from the polyisocyanate, NCO/OH=0.8:1–1.4:1 is preferable.

The polyether polyol compound represented by $R_1$—$[(O—R^2)_k—OH]_m$ preferably used to obtain the hydrophobically modified polyether polyurethane of general formula (1) can be obtained by addition polymerization of m-hydric polyol with an alkylene oxide such as ethylene oxide, propylene oxide, butylene oxide, or epichlorohydrin, styrene oxide, etc.

For this m-hydric polyol, di- to octa-hydric ones are preferable; examples include dihydric alcohols such as ethylene glycol, propylene glycol, butylene glycol, hexamethylene glycol, neopentyl glycol; trihydric alcohols such as glycerin, trioxy isobutane, 1,2,3-butanetriol, 1,2,3-pentatriol, 2-methyl-1,2,3-propanetriol, 2-methyl-2,3,4-butanetriol, 2-ethyl-1,2,3-butanetriol, 2,3,4-pentane triol, 2,3,4-hexanetriol, 4-propyl-3,4,5-heptanetriol, 2,4-dimethyl-2,3,4-pentanetriol, pentamethyl glycerin,pentaglycerin, 1,2,4-butanetriol, 1,2,4-pentanetriol, trimethylol ethane, and trimethylolpropane; tetrahydric alcohols such as pentaerythritol, 1,2,3,4-pentane tetrol, 2,3,4,5-hexane tetrol, 1,2,4,5-pentane tetrol, and 1,3,4,5-hexane tetrol; pentahydric alcohols such as adonitol, arabite, and xylitol; hexahydric alcohols such as dipentaerythritol, sorbitol, mannite, and iditol; and octahydric alcohols such as sucrose.

In addition, $R^2$ is determined by the alkylene oxide, styrene oxide and such to be added; alkylene oxides or styrene oxides having 2–4 carbon atoms are preferable for superior effects and easy procurement.

The alkylene oxide, styrene oxide and such to be added can be prepared by single polymerization, block polymerization or random polymerization of two or more kinds. A conventional method can be used for the addition. The degree of polymerization k is 0–1,000, preferably 1–500, and more preferably 10–50. When the ratio of the ethylene group in $R^2$ is 50–100 wt % of the total $R^2$, an associative thickener suitable for this purpose can be obtained.

The molecular weight of $R^1$—$[(O—R^2)_k—OH]_m$ is preferably 500–100,000, and more preferably 1,000–50,000.

Selection of the polyisocyanate represented by $R^3$—$(NCO)_{h+1}$ which is preferably used to obtain the hydrophobically modified polyether polyurethane of general formula (1) is not limited in particular as long as it has two or more isocyanate groups in the molecule. Examples include aliphatic diisocyanate, aromatic diisocyanate, alicycle diisocyanate, biphenyl diisocyanate, diisocyanate of phenylmethane, triisocyanate, and tetraisocyanate.

Examples of the aliphatic diisocyanate include: methylene diisocyanate, dimethylene diisocyanate, trimethylene diisocyanate, tetramethylene diisocyanate, pentamethylene diisocyanate, hexamethylene diisocyanate, dipropyl ether diisocyanate, 2,2-dimethylpentane diisocyanate, 3-methoxy hexane diisocyanate, octamethylene diisocyanate, 2,2,4-trimethylpentane diisocyanate, nonamethylene diisocyanate, decamethylene diisocyanate, 3-butoxy hexane diisocyanate, 1,4-butylene glycol dipropyl ether diisocyanate, thiodihexyl diisocyanate, metaxylylene diisocyanate, para xylylene diisocyanate, and tetramethyl xylylene diisocyanate.

Examples of the aromatic diisocyanate include: meta phenylene diisocyanate, paraphenylene diisocyanate, 2,4-tolylene diisocyanate, 2,6-tolylene diisocyanate, dimethylbenzene diisocyanate, ethyl benzene diisocyanate, isopropyl benzene diisocyanate, tolidine diisocyanate, 1,4-naphthalene diisocyanate, 1,5-naphthalene diisocyanate, 2,6-naphthalene diisocyanate, and 2,7-naphthalene diisocyanate.

Examples of the alicycle diisocyanate include: hydrogenated xylylene diisocyanate and isophorone diisocyanate.

Examples of the biphenyl diisocyanate include: biphenyl diisocyanate, 3,3'-dimethylbiphenyl diisocyanate, and 3,3'-dimethoxy biphenyl diisocyanate.

Examples of the diisocyanate of phenylmethane include: diphenyl-methane-4,4'-diisocyanate, 2,2'-dimethyl diphenyl-methane-4,4'-diisocyanate, diphenyl dimethylmethane-4,4'-diisocyanate, 2,5,2',5'-tetramethyl diphenyl-methane-4,4'-diisocyanate, cyclohexylbis(4-isocyanate phenyl) methane, 3,3'-dimethoxy diphenyl-methane-4,4'-diisocyanate, 4,4'-dimethoxy diphenyl-methane-3,3'-diisocyanate, 4,4'-diethoxy diphenyl-methane-3,3'-diisocyanate, 2,2'-dimethyl-5,5'-dimethoxy diphenyl-methane-4,4'-diisocyanate, 3,3'-dichloro diphenyl dimethylmethane-4,4'-diisocyanate, and benzophenone-3,3'-diisocyanate.

Examples of the triisocyanate include: 1-methylbenzene-2,4,6-triisocyanate, 1,3,5-trimethyl benzene-2,4,6-triisocyanate, 1,3,7-naphthalene triisocyanate, biphenyl-2,4,4'-triisocyanate, diphenyl-methane-2,4,4'-triisocyanate, 3-methyl diphenyl-methane-4,6,4'-triisocyanate, triphenylmethane-4,4',4''-triisocyanate, 1,6,11-undecane triisocyanate, 1,8-diisocyanate-4-isocyanate methyl octane, 1,3,6-hexamethylene triisocyanate, bicyclo heptane triisocyanate, and tris (isocyanate phenyl)thiophosphate.

Dimers and trimers (isocyanurate bonds) of these polyisocyanate compounds can also be used; biuret obtained by a reaction with an amine can also be used. Furthermore, polyisocyanate having a urethane bond obtained by a reaction between these polyisocyanates and a polyol can also be used. For the polyol, di-to octa-hydric ones are preferable; the aforementioned polyols are preferable. When tri-or-higher-hydric polyisocyanate is used for the $R^3$—$(NCO)_{h+1}$, this polyisocyanate having a urethane bond is preferable.

Selection of the polyether monoalcohol represented by HO—$(R^4—O)_n$—$R^5$ which is preferably used to obtain the hydrophobic polyether polyurethane of general formula (1) is not limited in particular as long as it is a polyether of a straight chain or branched chain secondary monohydric alcohol.

Such a compound can be obtained by addition polymerization of a secondary monohydric alcohol with an alkylene oxide such as ethylene oxide, propylene oxide, butylene oxide, and epichlorohydrin, styrene oxide, etc.

The straight chain alcohol mentioned here is represented by the following general formula (7).

The branched chain alcohol is represented by the following general formula (8).

The secondary alcohol is represented by the following general formula (9).

Therefore, $R^5$ is a group derived by removing a hydroxide group from the aforementioned general formulas (7)–(9). In the aforementioned general formulas (7)–(9), $R^6$, $R^7$, $R^8$, $R^{10}$, and $R^{11}$ are hydrocarbon groups.

In the aforementioned general formula (8), $R^9$ is a hydrocarbon group.

$R^5$ is a hydrocarbon group having 24 or more carbon atoms, preferably an alkyl group; among them, those with a total number of carbon atoms of 24 are more preferable, and hydrocarbon groups derived from decyltetradecyl alcohol are particularly preferable.

The present invention is based on a discovery of an unexpected effect of a length of the alkyl chain of $R^5$ that is 24 or more carbon atoms.

That is, when a hydrophobic polyether urethane acts as an associative thickener, the hydrophobic association is enhanced when $R^5$ has 24 or more carbon atoms, which in turn effectively increases the viscosity of the hair treatment agent composition containing a cationic surfactant.

The alkylene oxide, styrene oxide and such to be added can be prepared by single polymerization, block polymerization or random polymerization of two or more kinds. A conventional method can be used for the addition. The degree of polymerization k is 0–1,000, preferably 1–200, and more preferably 10–50. When the ratio of the ethylene group in $R^4$ is 50–100 wt %, preferably 65–100 wt %, of the total $R^4$, an associative thickener suitable for the object of the present invention can be obtained.

The compound represented by the aforementioned general formula (1) can be obtained by, for example, heating at 80–90° C.for 1–3 hours to bring the ingredients into reaction, in the same manner as in a usual reaction between polyether and isocyanate.

When the polyetherpolyols represented by $R^1$—[(O—$R^2)_k$—OH]$_m$ (a), the polyisocyanates represented by $R^3$—(NCO)$_{h+1}$ (b), and the polymonoalcohol represented by HO—($R'$—O)$_n$—$R^5$ (c) are brought into reaction, there may be byproducts other than the compound with a structure represented by general formula (1). For example, when diisocyanate is used, the main product will be the c-b-a-b-c type compound represented by general formula (1), but the c-b-c type, the c-b-(a-b)$_x$-a-b-c type and such may also be produced as byproducts. In such cases, the mixture containing the general formula (1) type compound can be used in the present invention without isolating the general formula (1) type compound.

1. A Hair treatment Agent Composition

The hair treatment agent composition of the present invention should preferably contain 0.1–10 wt % of the aforementioned hydrophobically modified polyether polyurethane. If the blend ratio is less than 0.1 wt % then the effect of the addition may not be observed; if it is higher than 10 wt % then the viscosity becomes too high, causing problems in handling during preparation, sometimes resulting in a reduction in the operation efficiency, problems in extracting the product from the container during actual use, and/or poor spreading at the time of application on the hair.

(B) Cationic surfactant (B) ingredient, i.e. the cationic surfactant, is described in detail below.

Selection of the Cationic Surfactant used in the Present Invention is not Limited in Particular; a Quartenary Ammonium Salt Represented by the Aforementioned General Formula (2) and an Amidoamine Type Compound Represented by the General Formula (3) are Preferably Used.

Specific examples of the quartenary ammonium salt represented by general formula (2) include: cetyltrimethylammonium chloride, stearyltrimethylammonium chloride, behenyl trimethylammonium chloride, behenyl dimethyl hydroxyethyl ammonium chloride, stearyldimethylbenzylammonium chloride, and cetyltriethylammonium methylsulfate; in particular, stearyldimethylammonium chloride, cetyltrimethylammonium chloride or behenyltrimethylammonium chloride is preferably used.

Specific examples of the amidoamine-type compound represented by general formula (3) include: stearamidoethyl diethylamine, stearamidoethyl dimethylamine, palmitamidoethyl diethylamine, palmitamidoethyl dimethylamine, myristamidoethyl diethylamine, myristamidoethyl dimethylamine, behenamidoethyl diethylamine, behenamidoethyl dimethylamine, stearamidopropyl diethylamine, stearamidopropyl dimethylamine, palmitamidopropyl diethylamine, palmitamidopropyl dimethylamine, myristamidopropyl diethylamine, myristamidopropyl dimethylamine, behenamidopropyl diethylamine, behenamidopropyl dimethylamine; in particular, stearamidoethyl diethylamine, stearamidopropyl dimethylamine, and behenamidopropyl dimethylamine are preferably used.

The blend ratio of the cationic surfactant is preferably 0.01–10 wt % of the total amount of the hair treatment agent composition. If the blend ratio is less than 0.01 wt % then smooth hair cannot be obtained. If the blend ratio is higher than 10 wt % then the solubility of the surfactant is not sufficient and precipitation may occur due to the concentration exceeding the saturation level; also, the conditioning effect is no longer dependent on the concentration, making it meaningless to add more.

In addition, the hair treatment agent composition of the present invention should preferably contain a higher alcohol and/or higher fatty acid.

Specific examples of the higher alcohol include: straight chain alcohols such as decanol, lauryl alcohol, cetyl alcohol, stearyl alcohol, behenyl alcohol, myristyl alcohol, oleyl alcohol, and cetostearyl alcohol, as well as branched chain alcohols such as monostearyl glycerin ether (batyl alcohol), 2-decyl tetradecyl alcohol, lanolin alcohol, cholesterol, phytosterol, hexyl dodecanol, isostearyl alcohol, and octyl dodecanol; in particular, cetyl alcohol,stearyl alcohol, and behenyl alcohol are preferably used.

Specific examples of the higher fatty acids include: capric acid, lauric acid, myristic acid, palmitic acid, stearic acid, behenic acid, oleic acid, 12-hydroxystearic acid, undecylenic acid, tall oil, isostearic acid, linolic acid, linolenic acid, eicosapentaenoic acid, and docosahexaenoic acid; in particular, stearic acid, palmitic acid, myristic acid, oleic acid, isostearic acid, 12-hydroxystearic acid, and behenic acid are preferably used.

The blend ratio of the aforementioned higher alcohol and/or higher fatty acid should preferably be such that the molar ratio of the cationic surfactant and the higher alcohol and/or higher fatty acid is 1:2–1:10, more preferably 1:3–1:5.

"Viscosity"

The viscosity of the hair treatment agent composition of the present invention is preferably 1–10 Pa·s as measured at 25° C. and $1s^{-1}$ or 0.1–1 Pa·s as measured at 25° C. and $100s^{-1}$. Preferably, both conditions should be met.

For the measurement conditions of 25° C. and $1s^{-1}$ (low shear rate), the aforementioned high viscosity range is preferable. If the viscosity is outside of the aforementioned range, then extracting the product from the container becomes difficult and spreading may become poor, resulting in problems during use.

For the measurement conditions of 25° C. and $100s^{-1}$ (high shear rate), the aforementioned high viscosity range is preferable.

If the viscosity is outside of the aforementioned range, then dripping occurs during use when the hair treatment agent composition is put in a hand and the composition gives the impression of being thin, making it difficult to give a so-called "rich" tactile sensation.

The aforementioned viscosity can be easily achieved by the specific hydrophobically modified polyether polyurethane of general formula (1).

The viscosity can be measured by using a commercial cone/plate type or concentric cylinder type viscometer: for example, CSL-100 from Carri-Med Co. Ltd.

"Other Additives"

In addition to the aforementioned essential ingredients, other ingredients normally used in hair treatment agents are blended as necessary in the hair treatment agent composition of the present invention within the range that does not affect the effect of the present invention; examples of such ingredients include propylene glycol, sorbitol, humectants such as glycerin, surfactants, conditioning agents such as silicone derivatives, active agents, humectants, chelating agents, pH regulators, antiinflammatory agents, preservatives, ultraviolet absorbents, antioxidants, pigments, and perfume; and preparation is conducted for the target formulation and application with a conventional method.

The pH of the hair treatment agent composition can be freely adjusted by using, for example, inorganic acids such as phosphoric acid, hydrochloric acid, and sulfuric acid as well as their salts, organic acids such as citric acid, malic acid, tartaric acid, and oxalic acid, as well as their salts, inorganic bases such as sodium hydroxide, potassium hydroxide, calcium hydroxide, and ammonia as well as their salts, and organic bases such as triethanolamine and its salt. The pH is not limited, but preferably adjusted to 2–7, more preferably 3–6.

We discovered that organic acid has the following unexpected effects on the composition of the present invention.
① Reduced color loss of dyed hair
② Tightening of hair cuticles and giving gloss to hair
These effects are particularly prominent when tartaric acid or glutamic acid is used for the organic acid.

The hair treatment agent composition of the present invention is preferably used as a hair conditioning agent such as a hair rinse, hair treatment, hair conditioner, hair pack, or conditioning shampoo.

2. A Cleaning Agent Composition

The cleaning agent composition of the present invention should preferably contain 0.1–10 wt % of the aforementioned hydrophobically modified polyether polyurethane. If the blend ratio is less than 0.1 wt % then the effect of the addition may not be observed; if it is higher than 10 wt % then the viscosity becomes too high, causing problems in handling during preparation, sometimes resulting in a reduction in the work efficiency, problems in extracting the product from the container during actual use, and/or poor spreading at the time of application on the hair.

(B) Anionic surfactant and/or ampholytic surfactant

The surfactant, (B) ingredient, is described in detail below.

"Anionic Surfactant"

The anionic surfactant used in the present invention is not limited in particular; preferable examples include anionic surfactants represented by the aforementioned general formulas (4), (5), and (6) Examples of (4) include cocoyl N-methyl taurate, lauryl methyl taurate, myristyl methyl taurate, sodium cocoyl taurate, and cocoyl isethionate; examples of (5) include lauroyl glutamate monosalt, lauroyl glutamate disalt, myristoyl glutamate monosalt, myristoyl glutamate disalt, cocoacyl glutamate monosalt, cocoacyl glutamate disalt, and cocoacyl glycinate; and examples of (6) include higher fatty acid salts such as laurate, myristate, and cocoyl salt.

Examples of M1, M2, M3, and M4 in these general formulas (4), (5), and (6) include sodium, potassium, ammonium, triethanolamine, and sodium N-methyl taurate. One, two, or more of these anionic surfactants can be used.

"Ampholytic Surfactant"

Selection of the ampholytic surfactant used in the present invention is not limited in particular; examples include the betaine type ampholytic surfactant such as lauryl dimethylaminoacetic betaine, myristylaminoacetic betaine, and cocoylamidopropyl betaine, and the imidazoline type ampholytic surfactants such as 2-cocoyl-N-carboxymethyl-N-hydroxyethyl imidazolinium betaine and 2-lauryl-N-carboxymethyl-N-hydroxyethyl imidazolinium betaine. One, two, or more of these ampholytic surfactants can be used.

When both of the aforementioned anionic surfactants and ampholytic surfactants are used, a preferable weight ratio is 10:0–2:8. If there is more of the ampholytic surfactant than indicated by the aforementioned ratio, foam formation and foam durability become inferior, which is not desirable for a cleaning agent composition.

The blend ratio of the cationic surfactant is preferably 5–40 wt % of the total amount of the cleaning agent composition. If the blend ratio is less than 5 wt % then foam formation is not sufficient and an adequate cleaning effect cannot be obtained. If the blend ratio is higher than 40 wt % then the solubility of the surfactant is not sufficient and precipitation may occur due to the concentration exceeding the saturation level; also, the cleaning effect is no longer dependent on the concentration, making it meaningless to add more.

"Viscosity"

The viscosity of the hair treatment agent composition of the present invention is preferably 1–10 Pa·s as measured at 25° C. and $1s^{-1}$ or 0.1–1 Pa·s as measured at 25° C. and $100s^{-1}$.

Preferably, both conditions should be met.

For the measurement conditions of 25° C. and 1s$^{-1}$ (low shear rate), the aforementioned high viscosity range is preferable. If the viscosity is outside of the aforementioned range, then extracting the product from the container becomes difficult and spreading may become poor, resulting in problems during use.

For the measurement conditions of 25° C. and 100s$^{-1}$ (high shear rate), the aforementioned high viscosity range is preferable.

If the viscosity is outside of the aforementioned range, then dripping occurs during use when the hair treatment agent composition is put in a hand and the composition gives the impression of being thin, making it difficult to give a so-called "rich" tactile sensation.

The aforementioned viscosity can be easily achieved by the specific hydrophobically modified polyether polyurethane of general formula (1).

The viscosity can be measured by using a commercial cone/plate type or concentric cylinder type viscometer: for example, CSL-100 from Carri-Med Co. Ltd.

"Other Additives"

In addition to the aforementioned essential ingredients, other ingredients normally used in cleaning agents are blended as necessary in the cleaning agent compositiont of the present invention within the range that does not affect the effect of the present invention; examples of such ingredients include humectants such as propylene glycol, sorbitol, and glycerin, surfactants, conditioning agents such as silicone derivatives, active agents, humectants, chelating agents, pH regulators, antiinflammatory agents, preservatives, ultraviolet absorbents, antioxidants, pigments, and perfume; and preparation is conducted for the target formulation and application with a conventional method.

We discovered that cationized starch has the following unexpected effects on the composition of the present invention.

① Superior smooth sensation at the time of rinsing
② No sticky hair

For the cationized starch, a commercial product (Sensomer CI-50: Nalco) is used; the blend ratio is usually 0.01–2 wt %, preferably 0.2–1.5 wt %, of the total amount of the composition.

EXAMPLES

The present invention is described in detail below by referring to Examples. The present invention is not limited to these Examples. The blend ratio is expressed in wt % units unless specified otherwise.

Prior to Examples, preparation examples of hydrophobically modified polyether polyurethane are shown below.

<Preparation Example A>

550 parts of polyethylene glycol (PEG) (molecular weight 11,000) (corresponds to $R^1$—[(O—$R^2$)$_k$—OH]$_m$) and 198 parts of an ethylene oxide (EO) 20-mole adduct of a branched alcohol (corresponds to $R^3$—(NCO)$_{h+1}$) represented by the following general formula (10) were put into a 100-ml four-mouth flask equipped with a thermometer, a nitrogen feed tube, and a stirrer,

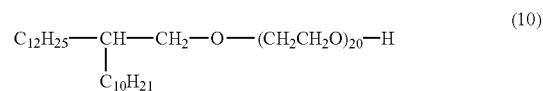

(10)

and then the mixture was cooled down to 80° C., after which 29.6 parts of hexamethylene diisocyanate (HMDI) (corresponds to $R^3$—(NCO)$_{h+1}$) was added, followed by a two-hour reaction in a nitrogen gas flow at 80–100° C.; after confirming that the isocyanate was 0%, the reaction product, consisting of light yellow solid matter at normal temperatures, was obtained.

Various kinds of hydrophobically modified polyether polyurethane can be prepared in a similar manner as in Preparation example A. For example, hydrophobically modified polyether polyurethane according to Preparation examples A–G shown in Table 1 is suitably used in the present invention.

TABLE 1

| | | Preparation example A | Preparation example B | Preparation example C | Preparation example D | Preparation example E | Preparation example F | Preparation example G |
|---|---|---|---|---|---|---|---|---|
| $R^1$ | | Ethylene | Ethylene | Ethylene | Ethylene | Dipenta-erythritol | Penta-erythritol | Ethylene |
| $R^2$ | | Ethylene | Ethylene | Ethylene | Ethylene | Ethylene | Ethylene | Ethylene |
| $R^3$ | | Hexa-methylene | Hexa-methylene | Hexa-methylene | Tetra-methylene | Tolylene | Xylylene | Trimethylol Propane-hexa-methylene |
| $R^4$ | | Ethylene | Ethylene | Ethylene | Propylene | Propylene | Ethylene | Ethylene |
| $R^5$ | | 2-decyl Tetradecyl | 2-decyl tetradecyl | 2-decyl tetradecyl | 2-decyl tetradecyl | 2-decyl tetradecyl | 2-decyl tetradecyl | 2-decyl tetradecyl |
| h | | 1 | 1 | 1 | 1 | 1 | 1 | 2 |
| m | | 2 | 2 | 2 | 2 | 6 | 4 | 2 |
| k | | 125 | 67 | 250 | 125 | 35 | 50 | 67 |
| n | | 20 | 10 | 20 | 20 | 10 | 20 | 100 |

In addition to the aforementioned Preparation examples, commercially available hydrophobically modified polyether polyurethane can also be used.

1. Examples of the hair treatment agent composition

Examples and Comparative examples shown in the tables were prepared with a conventional method. Using these samples, "tactile sensation at the time of application", "tactile sensation of hair after drying (smoothness and ease of arranging the hair)", and "temperature stability (viroscosity)" were evaluated according to the following evaluation methods.

Tactile Sensation at the time of Application

The sample was taken out of a container, an approximately 7 cm high plastic bottle with a one-touch cap on top, and used as a rinse; ease of application on the hair and comfortableness upon the application on the hair were evaluated by a panel of 20 specialists.

"Evaluation"

A: 18 or more panelists reported that ease of application or comfortableness upon the application on the hair was good.

B: 14–17 panelists reported that ease of application or comfortableness upon the application on the hair was good.

C: 8–13 panelists reported that ease of application or comfortableness upon the application on the hair was good.

D: 7 or less panelists reported that ease of application or comfortableness upon the application on the hair was good.

Tactile Sensation of Hair after Drying (Smoothness and Ease of Arranging the Hair)

After shampooing, 4 g of the prepared rinse was applied and rinsed away; after drying with a dryer, a panel of 20 specialists evaluated smoothness and ease of arranging the hair.

"Evaluation"

A: 18 or more panelists reported that smoothness and ease of arranging the hair were good.

B: 14–17 panelists reported that smoothness and ease of arranging the hair were good.

C: 8–13 panelists reported that smoothness and ease of arranging the hair were good.

D: 7 or less panelists reported that smoothness and ease of arranging the hair were good.

Temperature Stability (Viscosity)

The prepared samples were put into 50-ml transparent glass tubes and stored in constant-temperature baths at 50° C., 37° C., 25° C., and 0° C.; after six months, the samples' condition (viscosity) was observed. A cone/plate type or concentric cylinder type viscometer was used for the viscosity mearurement, and the apparent viscosity at 25° C. and $1s^{-1}$, and $100s^{-1}$, was determined.

Evaluation was conducted as follows:

"Evaluation"

A: The change in the viscosity of each temperature sample was 10% or less compared with the initial viscosity (25° C.).

B: The change in the viscosity of each temperature sample was 20% or less compared with the initial viscosity (25° C.).

C: The change in the viscosity of each temperature sample was 30% or less compared with the initial viscosity (25° C.).

D: The change in the viscosity of each temperature sample was more than 30% compared with the initial viscosity (25° C.).

TABLE 1-2

"Examples 1-1 to 1-11: Rinse"

| Examples | 1-1 | 1-2 | 1-3 | 1-4 | 1-5 | 1-6 | 1-7 | 1-8 | 1-9 | 1-10 | 1-11 |
|---|---|---|---|---|---|---|---|---|---|---|---|
| Comparative example | | | | | | | | | | | |
| Stearyl trimethylammonium chloride | 0.3 | | 1.0 | | | | 0.005 | 0.01 | 5 | 10 | 12 |
| Behenyl trimethylammonium chloride | | 0.7 | | | | | | | | | |
| Stearamidomethyl dimethylamine | | | | 1.0 | 2.0 | 3.0 | | | | | |
| Stearyl alcohol | | | | 5.0 | 5.0 | | | | | | |
| Palmitic acid | 0.6 | 2.0 | 5.0 | | | 5.0 | 0.02 | 0.04 | 20 | 40 | 48 |
| Compound of preparation example A of the present invention | 0.1 | 1.0 | 3.0 | 0.1 | 1.0 | 3.0 | 0.1 | 0.1 | 0.1 | 0.1 | 0.1 |
| L-glutamic acid | | 0.01 | 0.2 | 0.6 | 0.9 | 1.8 | 0.2 | 0.2 | 0.2 | 0.2 | 0.2 |
| Purified water | To 100 | To 100 | To 100 | To 100 | To 100 | To 100 | To 100 | To 100 | To 100 | To 100 | To 100 |

TABLE 1-2-continued

"Examples 1-1 to 1-11: Rinse"

| Examples | 1-1 | 1-2 | 1-3 | 1-4 | 1-5 | 1-6 | 1-7 | 1-8 | 1-9 | 1-10 | 1-11 |
|---|---|---|---|---|---|---|---|---|---|---|---|
| Tactile sensation at the time of application | B | A | A | A | A | B | C | B | B | B | C |
| Tactile sensation of the hair after drying | B | A | A | A | A | B | B | B | A | A | A |
| Temperature stability | B | A | A | A | A | B | B | B | A | A | A |
| Viscosity (Pa·s) | | | | | | | | | | | |
| 25° C. $1S^{-1}$ | 0.78 | 1.8 | 9.8 | 2.2 | 5.6 | 12.4 | 0.44 | 0.82 | 15.0 | 16.4 | 29.0 |
| 25° C. $100S^{-1}$ | 0.10 | 0.12 | 0.37 | 0.15 | 0.30 | 0.44 | 0.10 | 0.11 | 0.48 | 0.77 | 1.0 |
| Mole ratio* | 1:2.7 | 1:4.4 | 1:6.8 | 1:6.8 | 1:3.4 | 1:2.4 | 1:5.4 | 1:5.4 | 1:5.4 | 1:5.4 | 1:5.4 |

TABLE 1-3

"Comparative examples 1-1 to 1-6: Rinse"

| Examples Comparative example | 1-1 | 1-2 | 1-3 | 1-4 | 1-5 | 1-6 |
|---|---|---|---|---|---|---|
| Stearyl trimethyl-ammonium chloride | 0.3 | | 1.0 | | | |
| Behenyl trimethyl-ammonium chloride | | 0.7 | | | | |
| Stearamido-methyl dimethylamine | | | | 1.0 | 2.0 | 3.0 |
| Stearyl alcohol | | | | 5.0 | 5.0 | |
| Palmitic acid | 0.6 | 2.0 | 5.0 | | | 5.0 |
| Compound of preparation example A of the present invention | | | | | | |
| L-glutamic acid | | 0.01 | 0.2 | 0.6 | 0.9 | 1.8 |
| Purified water | to 100 | to 100 | to 100 | to 100 | to 100 | to 100 |
| Tactile sensation at the time of application | D | D | D | C | C | D |
| Tactile sensation of the hair after drying | D | D | D | C | C | C |
| Temperature stability | D | D | D | C | C | C |
| Viscosity (Pa·s) | | | | | | |
| 25° C. $1S^{-1}$ | 0.22 | 0.18 | 0.16 | 0.45 | 0.40 | 0.29 |
| 25° C. $100S^{-1}$ | 0.08 | 0.07 | 0.07 | 0.09 | 0.09 | 0.08 |
| Mole ratio | 1:2.7 | 1:4.4 | 1:6.8 | 1:6.8 | 1:3.4 | 1:2.4 |

TABLE 1-4

"Examples 1-12 to 1-14 and Comparative examples 1-7 to 1-9: Conditioning shampoo"

| Examples / Comparative example | 1-12 | 1-13 | 1-14 | 1-7 | 1-8 | 1-9 |
|---|---|---|---|---|---|---|
| Sodium N-cocoyl-N-methyl taurate | 7.0 | 9.0 | 9.0 | 7.0 | 9.0 | 9.0 |
| Cocoyl amide propyldimethyl glycine | 7.0 | 3.0 | 3.0 | 7.0 | 3.0 | 3.0 |
| Stearyl trimethyl-ammonium chloride | | 0.12 | 0.15 | | 0.12 | 0.15 |
| Stearamido-methyl dimethylamine | 0.1 | | | 0.1 | | |
| Stearyl alcohol | 0.25 | 0.8 | 1.0 | 0.25 | 0.8 | 1.0 |
| Palmitic acid | | | 0.1 | | | 0.1 |
| Compound of preparation example A of the present invention | 0.3 | 0.5 | 1.0 | | | |
| Purified water | to 100 | to 100 | to 100 | to 100 | to 100 | to 100 |
| Tactile sensation at the time of application (shampoo) | A | A | A | C | C | C |
| Tactile sensation of the hair after drying | A | A | A | D | D | D |
| Temperature stability | A | A | A | D | D | D |
| Viscosity (Pa·s) | | | | | | |
| 25° C. $1S^{-1}$ | 2.5 | 4.6 | 9.0 | 0.47 | 0.40 | 0.25 |
| 25° C. $100S^{-1}$ | 0.16 | 0.30 | 0.40 | 0.09 | 0.09 | 0.08 |
| Mole ratio* | 1:3.4 | 1:8.6 | 1:9.5 | 1:3.4 | 1:8.6 | 1:9.5 |

The aforementioned investigation indicated that the hair treatment agent composition of the present invention is superior in tactile sensation at the time of application, tactile sensation of the hair after drying, and temperature stability.

TABLE 1-5

"Examples 1-15 to 1-20: Rinse"

| Examples | 1-15 | 1-16 | 1-17 | 1-18 | 1-19 | 1-20 |
|---|---|---|---|---|---|---|
| Comparative example | | | | | | |
| Stearyl trimethylammonium chloride | 1.0 | 1.0 | 1.0 | 1.0 | 1.0 | 1.0 |
| Behenyl trimethylammonium chloride | | | | | | |
| Stearamidomethyl dimethylamine | | | | | | |
| Stearyl alcohol | 3.0 | 3.0 | 3.0 | 3.0 | 3.0 | 3.0 |
| Palmitic acid | 1.0 | 1.0 | 1.0 | 1.0 | 1.0 | 1.0 |
| Compound of preparation example A of the present invention | 0.05 | 0.1 | 1.0 | 5.0 | 10.0 | 15.0 |
| L-glutamic acid | 0.1 | 0.1 | 0.1 | 0.1 | 0.1 | 0.1 |
| Purified water | to 100 | to 100 | to 100 | to 100 | to 100 | to 100 |
| Tactile sensation at the time of application | B | B | A | A | B | C |
| Tactile sensation of the hair after drying | B | B | A | A | A | B |
| Temperature stability | C | A | A | A | A | B |
| Viscosity (Pa·s) | | | | | | |
| 25° C. 1S$^{-1}$ | 0.72 | 0.98 | 1.6 | 7.0 | 12.3 | 29.0 |
| 25° C. 100S$^{-1}$ | 0.10 | 0.11 | 0.12 | 0.35 | 0.44 | 1.1 |
| Mole ratio* | 1:5.2 | 1:5.2 | 1:5.2 | 1:5.2 | 1:5.2 | 1:5.2 |

The aforementioned investigation indicated that the desirable blend ratio of the hydrophobically modified polyether polyurethane to be blended in the composition of the present invention is 0.1–10 wt %.

Also, results shown in Table 1-2-1-5 indicate that, in order to obtain superior tactile sensation at the time of application, the viscosity should preferably be 1–10 Pa·s as measured at 25° C. and 1s$^{-1}$ or 0.1–1 Pa·s as measured at 25° C. and 100s$^{-1}$.

TABLE 1-6

"Examples 1-21 and Comparative examples 1-10 to 1-12: Rinse"

| Examples | 1-21 | | | |
|---|---|---|---|---|
| Comparative example | | 1-10 | 1-11 | 1-12 |
| Stearyl trimethylammonium chloride | | | | |
| Behenyl trimethylammonium chloride | 1.0 | 1.0 | 1.0 | 1.0 |
| Stearamidomethyl dimethylamine | 0.1 | 0.1 | 0.1 | 0.1 |
| Stearyl alcohol | 3.0 | 3.0 | 3.0 | 3.0 |
| Palmitic acid | | | | |
| Compound of preparation example A of the present invention | 1.0 | | | |
| Carboxy vinyl polymer | | 1.0 | | |
| Xanthan gum | | | 1.0 | |
| PEG 11000 | | | | 1.0 |
| L-glutamic acid | 0.1 | 0.1 | 0.1 | 0.1 |
| Purified water | to 100 | to 100 | to 100 | to 100 |
| Tactile sensation at the time of application | A | C | B | D |
| Tactile sensation of the hair after drying | A | D | D | C |
| Temperature stability | A | D | C | D |
| Viscosity (Pa·s) | | | | |
| 25° C. 1S$^{-1}$ | 3.0 | 70.2 | 12.4 | 0.51 |
| 25° C. 100S$^{-1}$ | 0.17 | 3.0 | 0.79 | 0.09 |
| Mole ratio * | 1:4 | 1:4 | 1:4 | 1:4 |

The aforementioned investigation indicated that the composition of the present invention has superior characteristics compared with a composition containing a commonly-used polymer thickener.

TABLE 1-7

"Examples 1-22 to 1-27: Rinse"

| Examples | 1-22 | 1-23 | 1-24 | 1-25 | 1-26 | 1-27 |
|---|---|---|---|---|---|---|
| Comparative example | | | | | | |
| Stearyl trimethylammonium chloride | 0.1 | 0.1 | | 0.2 | 0.1 | 0.1 |
| Behenyl trimethylammonium chloride | 0.2 | 0.2 | | | | |
| Cetyltrimethylammonium chloride | 0.1 | 0.1 | | | | |
| Stearamidomethyl dimethylamine | | | 0.2 | 0.2 | 0.1 | 0.1 |
| Stearamidoethyl diethylamine | | | 0.1 | | 0.1 | 0.1 |
| Behenamidopropyl dimethylamine | | | 0.1 | | | |
| Cetyl alcohol | 0.2 | 0.3 | 0.2 | 0.9 | 1 | 1.2 |
| Stearyl alcohol | 0.2 | 0.3 | 0.5 | 0.6 | 0.7 | 0.9 |
| Behenyl alcohol | 0.2 | 0.3 | 0.5 | 0.6 | 0.5 | 0.6 |
| Palmitic acid | | | | | | |
| Stearic acid | | | | | | |
| Myristic acid | | | | | | |
| Oleic acid | | | | | | |
| Isostearic acid | | | | | | |
| 12-hydroxystearic acid | | | | | | |
| Behenic acid | | | | | | |
| Compound of preparation example A of the present invention | 0.2 | 0.2 | 0.2 | 0.2 | 0.2 | 0.2 |
| L-glutamic acid | | | | | | |
| Purified water | to 100 | to 100 | to 100 | to 100 | to 100 | to 100 |
| Tactile sensation at the time of application | B | B | A | A | B | C |
| Tactile sensation of the hair after drying | C | A | A | A | A | B |

TABLE 1-7-continued

"Examples 1-22 to 1-27: Rinse"

| Examples | 1-22 | 1-23 | 1-24 | 1-25 | 1-26 | 1-27 |
|---|---|---|---|---|---|---|
| Temperature stability | B | B | A | A | A | B |
| Viscosity (Pa · s) | | | | | | |
| 25° C. $1S^{-1}$ | 0.66 | 0.93 | 3.4 | 8.0 | 14.1 | 24.1 |
| 25° C. $100S^{-1}$ | 0.10 | 0.11 | 0.16 | 0.41 | 0.49 | 1.12 |
| Mole ratio * | 1:2 | 1:3 | 1:4 | 1:5 | 1:10 | 1:12 |

The aforementioned investigation shows that the molar ratio of the cation surfactant and the higher alcohol and/or higher fatty acid is preferably 1:2–1:10 for the composition of the present invention.

TABLE 1-8

"Examples 1-28 to 1-33: Rinse"

| Examples | 1-28 | 1-29 | 1-30 | 1-31 | 1-32 | 1-33 |
|---|---|---|---|---|---|---|
| Comparative example | | | | | | |
| Stearyl trimethylammonium chloride | 0.1 | 0.1 | 0.1 | 0.1 | 0.1 | 0.1 |
| Behenyl trimethylammonium chloride | | | | | | |
| Cetyltrimethylammonium chloride | | | | | | |
| Stearamidomethyl dimethylamine | 0.1 | 0.1 | 0.1 | 0.1 | 0.1 | 0.1 |
| Stearamidoethyl diethylamine | 0.1 | 0.1 | 0.1 | 0.1 | 0.1 | 0.1 |
| Behenamidopropyl dimethylamine | | | | | | |
| Cetyl alcohol | | | | | | |
| Stearyl alcohol | | | | | | |
| Behenyl alcohol | | | | | | |
| Palmitic acid | 0.1 | 0.2 | 0.1 | 0.2 | 0.5 | 0.5 |
| Stearic acid | 0.2 | 0.2 | 0.4 | 0.8 | 0.8 | 0.8 |
| Myristic acid | 0.1 | 0.2 | 0.1 | 0.2 | 0.3 | 0.3 |
| Oleic acid | | | 0.1 | 0.2 | 0.2 | 0.3 |
| Isostearic acid | | | 0.1 | 0.2 | 0.2 | 0.3 |
| 12-hydroxystearic acid | | | 0.05 | 0.1 | 0.1 | 0.3 |
| Behenic acid | | | 0.05 | 0.1 | 0.1 | 0.3 |
| Compound of preparation example A of the present invention | 0.2 | 0.2 | 0.2 | 0.2 | 0.2 | 0.2 |
| L-glutamic acid | | | | | | |
| Purified water | to 100 | to 100 | to 100 | to 100 | to 100 | to 100 |
| Tactile sensation at the time of application | B | B | A | A | B | C |
| Tactile sensation of the hair after drying | C | A | A | A | A | B |
| Temperature stability | B | B | A | A | A | B |
| Viscosity (Pa · s) | | | | | | |
| 25° C. $1S^{-1}$ | 0.76 | 0.81 | 3.6 | 7.6 | 15.3 | 22.2 |
| 25° C. $100S^{-1}$ | 0.11 | 0.11 | 0.14 | 0.34 | 0.50 | 1.2 |
| Mole ratio * | 1:2 | 1:3 | 1:4 | 1:5 | 1:10 | 1:12 |

The aforementioned investigation indicated that the composition of the present invention has superior characteristics compared with a composition containing a commonly-used polymer thickener.

The following test was conducted to verify the unexpected effect of the present invention.

"Effect of $R^5$ on General Formula (1)"

It was confirmed that the hydrophobic association of the associative thickener of general formula (1) is enhanced by lengthening of the chain of the end hydrophobic group and the system can be thickened more effectively.

A cone/plate type or concentric cylinder type viscometer was used for the viscosity mearurement, and the apparent viscosity at 25° C. and $1s^{-1}$, and $100s^{-1}$, was determined.

TABLE 1-9

| $R^5$ Number of carbon atoms*[1] | Viscosity of 1% simple aqueous solution (Pa · s) | | Viscosity of the rinse*[2] (Pa · s) | |
|---|---|---|---|---|
| | 25° C. $1S^{-1}$ | 25° C. $100S^{-1}$ | 25° C. $1S^{-1}$ | 25° C. $100S^{-1}$ |
| 12 | 0.06 | 0.04 | 1.5 | 1.4 |
| 16 | 0.40 | 0.12 | 3.0 | 0.24 |
| 18 | 1.2 | 0.15 | 4.6 | 0.32 |
| 24 | 3.8 | 0.18 | 9.8 | 0.53 |

*[1]Associative thickeners (hydrophobically modified polyether urethane) with different numbers of carbons in $R^5$ were prepared in a similar manner as in Preparation example A.

The compound having 24 carbon atoms is the hydrophobically modified polyether urethane of Preparation example A.

The compound having 18 carbon atoms was prepared by using EO 20-mole adduct of stearyl alcohol for the compound corresponding to general formula (10) of Preparation example A.

The compound having 16 carbon atoms was prepared by using EO 20-mole adduct of cetyl alcohol for the compound corresponding to general formula (10) of Preparation example A.

The compound having 16 carbon atoms was prepared by using EO 20-mole adduct of lauryl alcohol for the compound corresponding to general formula (10) of Preparation example A.

| *[2]Rinse recipe | |
|---|---|
| Stearyl trimethylammonium chloride | 2 wt % |
| Stearyl alcohol | 6 wt % |
| Associative thickener shown in the table | 1 wt % |
| Ion-exchange water | Balance |

The aforementioned investigation shows that the thickening effect is enhanced not only in the simple aqueous solution but also in the hair treatment agent composition of the present invention when hydrophobically modified polyether urethane whose $R^5$ has 24 carbon atoms was used.

"Effect of Blending Organic Acid"

It was verified that the addition of organic acid reduces color loss of dyed hair, tightens cuticles and gives gloss to the hair.

The test was conducted by using a rinse prepared with the following recipe.

| | |
|---|---|
| Stearyl trimethylammonium chloride | 2 wt % |
| Stearyl alcohol | 6 wt % |
| Compound of preparation example A | 1 wt % |
| Organic acid (salt) shown in the table | 0 or 0.5 wt % |
| Ion-exchange water | Balance |

TABLE 1-10

| Test item | Not added | Citric acid | Tartaric acid | Glutamic acid | Sodium citrate |
|---|---|---|---|---|---|
| Color loss of dyed hair*[1] | 3.0 | 1.2 | 1.1 | 0.9 | 2.9 |
| Gloss of hair*[2] | — | ○ | ○ | ○ | x |

*[1]Bleached hair strands were dyed with a commercial acidic hair dye. The dyed hair was washed with a commercial shampoo and then the aforementioned rinse was applied on it, followed by rinsing with tap water and drying with a dryer. The aforementioned procedure was repeated five times and the color difference of the hair between before and after the treatment was measured using a color analyzer with the reflection method. The color difference ($\Delta E$) is listed in the table.
*[2]Goniophotometer GP-200 (from Murakami Color Research Laboratory) was used; eleven hairs with their directions at the hair tip and the base aligned together were irradiated with an incident angle of 30 degrees and the quantity of reflected light was measured at varied angles from 0 to 90 degrees.

Equation 1

Gloss=Mirror Reflection of the Maximum Peak (S)÷Maximum Diffusion Peak in the Direction of the Normal Line of the Sample (D)

The gloss was determined with the above equation (S/D).

Those which had a gloss equivalent to or lower than that of "Not added" were designated as "x". Those which had a gloss higher than that of "Not added" were designated as "○".

The aforementioned test shows that the addition of an organic acid suppresses color loss of dyed hair and increases the gloss of hair.

Additional Examples of the present invention are shown below. In all of the following Examples, the hydrophobically modified polyether urethane is a commercial product (Adecanol GT-700 from Asahi Denka Kogyo).

Example 1–34

Treatment Hair Pack

| | Wt % |
|---|---|
| Purified water | Balance to make the total of 100 weight parts |
| Cetostearyl alcohol | 7.00 |
| Behenyl alcohol | 5.00 |
| Dimethyl polysiloxane 1000cs | 2.00 |
| Cetyl isooctanoate | 1.00 |
| Stearamidoethyl dimethylamine | 3.00 |
| DL-glutamic acid | Amount needed to adjust the system pH to 4.2 |
| Soy bean lecithin | 0.10 |
| Isoprene glycol | 5.00 |
| Hydrophobically modified polyether polyurethane | 0.50 |
| Methylparaben | 0.20 |
| Disodium edetate | 0.01 |
| Phenoxyethanol | 0.20 |
| Blending perfume | 0.50 |

Purified water was heated up and the higher alcohol and other oil ingredients were added, followed by vigorous stirring. Glutamic acid was added to the system to lower the pH and turn the system into an emulsion; other ingredients were added and, after stirring and mixing, a high efficiency disperser was used to adjust the particle size of the oil ingredients to 5 micrometers or less, followed by rapid cooling by a heat exchanger to obtain a treatment hair pack.

Example 1–35

Hair Conditioner

| | Wt % |
|---|---|
| Purified water | Balance to make the total of 100 weight parts |
| Cationic polymer (Nalco Chemical Company; Merquat 550) | 1.00 |
| Cetostearyl alcohol | 2.50 |
| Behenyl alcohol | 2.00 |
| Partially amino-modified dimethyl polysiloxane 50000cs | 0.20 |
| Partially polyoxyethylene modified dimethyl polysiloxane 100cs | 0.20 |
| Dimethyl polysiloxane 20cs | 1.80 |
| Isononyl isononanoate | 0.50 |
| 12-hydroxystearic acid | 0.50 |
| Stearamidoethyl dimethylamine | 0.80 |
| DL-glutamic acid | Amount needed to adjust the system pH to 4.2 |
| Dipotassium glycyrrhizate | 0.10 |
| Isoprene glycol | 3.00 |
| Hydrophobically modified polyether polyurethane | 0.50 |
| Methylparaben | 0.20 |
| Seaweed extract | 0.10 |
| Phenoxyethanol | 0.20 |
| Blended perfume | 0.50 |

Purified water was heated up and the higher alcohol and other oil ingredients were added, followed by vigorous stirring. Silicones were mixed in a separate vessel and then added. Glutamic acid was added to the system to lower the pH and turn the system into an emulsion; other ingredients were added and, after stirring and mixing, a high efficiency disperser was used to adjust the particle size of the oil ingredients to 3 micrometers or less, followed by rapid cooling by a heat exchanger to obtain a hair conditioner.

Example 1–36

Hair Conditioner

|  | Wt % |
| --- | --- |
| Purified water | Balance to make the total of 100 weight parts |
| Cationic polymer (Nalco Chemical Company; Merquat 550) | 1.00 |
| Cetostearyl alcohol | 1.00 |
| Behenyl alcohol | 2.00 |
| Polyoxyethylene (3) stearyl ether | 0.20 |
| Dimethyl polysiloxane 6cs | 1.80 |
| Isocetyl isostearate | 0.50 |
| Stearyl trimethylammonium chloride | 0.70 |
| Succinic acid | Amount needed to adjust the system pH to 4.2 |
| Non-heat coagulated egg white | 0.01 |
| Hydrogenated egg yolk oil | 0.01 |
| Vitamin E acetate | 0.01 |
| Soy bean extract | 0.10 |
| Propylene glycol | 10.00 |
| Hydrophobically modified polyether polyurethane | 0.50 |
| Methylparaben | 0.20 |
| Phenoxyethanol | 0.20 |
| Blended perfume | 0.50 |

Purified water was heated up and the higher alcohol and other oil ingredients were added, followed by vigorous stirring. Succinic acid was added to the system to lower the pH and turn the system into an emulsion; other ingredients were added and, after stirring and mixing, a high efficiency disperser was used to adjust the particle size of the oil ingredients to 3 micrometers or less, followed by rapid cooling by a heat exchanger to obtain a hair conditioner.

2. Examples of the cleaning agent composition

The following Examples and Comparative examples were prepared with a conventional method. Using these samples, "temperature stability" (visocosity), "visco-elasticity" (sensory evaluation of the viscosity of the product), "foam formation", "foam durability" and "refreshing sensation during cleaning" of the cleaning agent were evaluated according to the following evaluation methods.

Temperature Stability (Viscosity)

The prepared samples were put into 50-ml transparent glass tubes and stored in constant-temperature baths at 50° C., 37° C., 25° C., and 0° C.; after six months, the samples' condition (viscosity) was observed. A cone/plate type or concentric cylinder type viscometer was used for the viscosity mearurement, and the apparent viscosity at 25° C. and $1s^{-1}$, and $100s^{-1}$ was determined. Evaluation was conducted as follows:

"Evaluation"

⊚: The change in the viscosity of each temperature sample was 10% or less compared with the initial viscosity (25° C.).

○: The change in the viscosity of each temperature sample was 20% or less compared with the initial viscosity (25° C.).

Δ: The change in the viscosity of each temperature sample was more than 20% compared with the initial viscosity (25° C.).

Visco-elasticity (Sensory Evaluation of the Product Viscosity)

Each sample was extracted from a 50-ml transparent glass tube onto a hand and dripping from the hand and ease of spreading were evaluated by a panel of 20 people. Evaluation was conducted based on the following criteria:

"Evaluation"

⊚: 15 or more of the 20 people judged that the applicability at the time of cleaning was good (no dripping from the hand; good spreading when applied).

○: 11–14 of the 20 people judged that the applicability at the time of cleaning was good (no dripping from the hand; good spreading when applied).

Δ: 10 or less of the 20 people judged that the applicability at the time of cleaning was good (no dripping from the hand; good spreading when applied).

Foam Formation 400 ml of 40° C. artificial hard water (70 ppm calcium carbonate) was put into a 2,500 ml cylindrical container equipped with a stirrer, and 4 g of the prepared sample was added to it; the foam volume was measured immediately following stirring at 4,500 rpm for one minute.

"Evaluation"

⊚: Good foaming (foam volume 1,200 ml or more)

○: Fair foaming (foam volume 800 ml or more)

Δ: Poor foaming (foam volume less than 800 ml)

Foam Durability

The foam volume was measured five minutes after the aforementioned foam formation measurement, and the ratio with the foam formation immediately following stirring was determined.

The ratio was calculated as (foam volume after 5 minutes/foam volume immediately following stirring).

"Evaluation"

⊚: Good foam durability (ratio 0.8 or higher)

○: Fair foam durability (ratio 0.6 or more and less than 0.8)

Δ: Poor foam durability (ratio less than 0.6)

Refreshing Sensation (Sensory Evaluation During Rinsing and after Towel-drying)

3 g of each sample was used for face washing and the refreshing sensation during rinsing and after towel-drying was evaluated by a panel of 20 people. Evaluation was conducted based on the following criteria:

"Evaluation"

⊚: 15 or more of the 20 people judged that there was a refreshing sensation during rinsing and after towel-drying.

○: 11–14 of the 20 people judged that there was a refreshing sensation during rinsing and after towel-drying.

Δ: 10 or less of the 20 people judged that there was a refreshing sensation during rinsing and after towel-drying.

TABLE 2-2

| | Examples | | | | Comparative example | | | |
|---|---|---|---|---|---|---|---|---|
| | 2-1 | 2-2 | 2-3 | 2-4 | 2-1 | 2-2 | 2-3 | 2-4 |
| Sodium cocoyl methyl taurate | 10.0 | — | — | — | 10.0 | — | — | — |
| Sodium cocoyl glutamate | — | 10.0 | — | — | — | 10.0 | — | — |
| Potassium laurate | — | — | 7.0 | — | — | — | 7.0 | — |
| Potassium myristate | — | — | 3.0 | — | — | — | 3.0 | — |
| Sodium cocoyl isethionate | — | — | — | 10.0 | — | — | — | 10.0 |
| Cocoyl amide propyldimethyl glycine | — | — | — | — | — | — | — | — |
| Preservative | Appropriate amount | Appropriate amount | Appropriate amount | Appropriate amount | Appropriate amount | Appropriate amount | Appropriate amount | Appropriate amount |
| Perfume | Appropriate amount | Appropriate amount | Appropriate amount | Appropriate amount | Appropriate amount | Appropriate amount | Appropriate amount | Appropriate amount |
| Hydrophobically modified polyether polyurethane described in preparation example (A) of the present invention | 1.0 | 1.0 | 1.0 | 1.0 | — | — | — | — |
| Purified water | to 100 | to 100 | to 100 | to 100 | to 100 | to 100 | to 100 | to 100 |
| Temperature stability (viscosity) | ⊚ | ⊚ | ⊚ | ⊚ | Δ | Δ | Δ | Δ |
| Viscoelasticity | ⊚ | ⊚ | ⊚ | ⊚ | Δ | Δ | Δ | Δ |
| Foam formation | ⊚ | ⊚ | ⊚ | ⊚ | ⊚ | ○ | ⊚ | ○ |
| Foam durability | ⊚ | ⊚ | ⊚ | ⊚ | ○ | ○ | ○ | ○ |
| Refreshing sensation | ⊚ | ⊚ | ⊚ | ⊚ | ○ | ○ | ○ | ○ |
| Viscosity (Pa · s) | | | | | | | | |
| 25° C. $1S^{-1}$ | 2.8 | 3.4 | 1.9 | 1.4 | 0.1 | 0.1 | 0.06 | 0.05 |
| 25° C. $100S^{-1}$ | 0.3 | 0.3 | 0.2 | 0.1 | 0.08 | 0.08 | 0.05 | 0.05 |

The aforementioned investigation indicates that the cleaning agent composition of the present invention has superior temperature stability, viscosity, foam formation, and foam durability. On the other hand, it has been shown that when the hydrophobically modified polyether urethane is not blended in, temperature stability and sensory evaluation results of the viscosity in particular are inferior.

TABLE 2-3

| | Examples | | Comparative example | | | |
|---|---|---|---|---|---|---|
| | 2-5 | 2-6 | 2-5 | 2-6 | 2-7 | 2-8 |
| Sodium cocoyl methyl taurate | 5.0 | 2.0 | 1.0 | 5.0 | 2.0 | 1.0 |
| Sodium cocoyl glutamate | — | — | — | — | — | — |
| Potassium laurate | — | — | — | — | — | — |
| Potassium myristate | — | — | — | — | — | — |
| Sodium cocoyl isethionate | — | — | — | — | — | — |
| Cocoyl amide propyldimethyl glycine | 5.0 | 8.0 | 9.0 | 5.0 | 8.0 | 9.0 |
| Preservative | Appropriate amount | Appropriate amount | Appropriate amount | Appropriate amount | Appropriate amount | Appropriate amount |
| Perfume | Appropriate amount | Appropriate amount | Appropriate amount | Appropriate amount | Appropriate amount | Appropriate amount |

TABLE 2-3-continued

| Examples | 2-5 | 2-6 | | | | |
| Comparative example | | | 2-5 | 2-6 | 2-7 | 2-8 |
|---|---|---|---|---|---|---|
| Hydrophobically modified polyether polyurethane described in preparation example (A) of the present invention | 1.0 | 1.0 | 1.0 | — | — | — |
| Purified water | to 100 | to 100 | to 100 | to 100 | to 100 | to 100 |
| Temperature stability (viscosity) | ◎ | ◎ | ◎ | △ | △ | △ |
| Visco-elasticity | ◎ | ○ | △ | △ | △ | △ |
| Foam formation | ◎ | ○ | △ | ○ | ○ | △ |
| Foam durability | ◎ | ◎ | ◎ | △ | △ | △ |
| Refreshing sensation | ◎ | ◎ | ○ | ○ | △ | △ |
| Viscosity (Pa · s) | | | | | | |
| 25° C. $1S^{-1}$ | 9.8 | 12.0 | 0.5 | 0.3 | 0.5 | 0.1 |
| 25° C. $100S^{-1}$ | 0.8 | 0.9 | 0.08 | 0.04 | 0.08 | 0.04 |

The above investigation shows that the cleaning agent composition of the present invention exhibits superior characteristics. On the other hand, it has been shown that the sensory evaluation of the viscosity and the foam formation become particularly poor when the weight ratio between the anionic surfactant and the ampholytic surfactant is higher than 2:8.

TABLE 2-4

| Examples Comparative example | 2-7 | 2-8 | 2-9 | 2-10 | 2-11 | 2-12 |
|---|---|---|---|---|---|---|
| Sodium cocoyl methyl taurate | 12.0 | 12.0 | 12.0 | 12.0 | 12.0 | 12.0 |
| Sodium cocoyl glutamate | — | — | — | — | — | — |
| Potassium laurate | — | — | — | — | — | — |
| Potassium myristate | — | — | — | — | — | — |
| Sodium cocoyl isethionate | — | — | — | — | — | — |
| Cocoyl amide propyldimethyl glycine | 6.0 | 6.0 | 6.0 | 6.0 | 6.0 | 6.0 |
| Preservative | Appropriate amount | Appropriate amount | Appropriate amount | Appropriate amount | Appropriate amount | Appropriate amount |
| Perfume | Appropriate amount | Appropriate amount | Appropriate amount | Appropriate amount | Appropriate amount | Appropriate amount |
| Hydrophobically modified polyether polyurethane described in preparation example (A) of the present invention | 0.05 | 0.1 | 1.0 | 5.0 | 10.0 | 12.0 |
| Purified water | to 100 | to 100 | to 100 | to 100 | to 100 | to 100 |
| Temperature stability (viscosity) | ○ | ◎ | ◎ | ◎ | ◎ | ◎ |
| Visco-elasticity | ○ | ○ | ◎ | ◎ | ○ | △ |
| Foam formation | ◎ | ◎ | ◎ | ◎ | ○ | ○ |
| Foam durability | ○ | ○ | ◎ | ◎ | ◎ | ◎ |
| Refreshing sensation | ○ | ◎ | ◎ | ◎ | ◎ | ○ |
| Viscosity (Pa · s) | | | | | | |
| 25° C. $1S^{-1}$ | 0.6 | 1.0 | 209 | 10.0 | 19.3 | 29.4 |
| 25° C. $100S^{-1}$ | 0.1 | 0.2 | 0.3 | 0.5 | 0.8 | 1.1 |

The above investigation shows that the best blend ratio of the hydrophobically modified polyether urethane in the cleaning agent composition of the present invention is 0.1–10 wt %.

TABLE 2-5

| Examples Comparative example | 2-13 | 2-14 | 2-15 | 2-16 | 2-17 |
|---|---|---|---|---|---|
| Sodium cocoyl methyl taurate | 2.0 | 4.0 | 16.0 | 30.0 | 40.0 |
| Sodium cocoyl glutamate | 0.5 | 0.5 | 0.5 | 0.5 | 0.5 |
| Potassium laurate | — | — | — | — | — |
| Potassium myristate | — | — | — | — | — |
| Sodium cocoyl isethionate | — | — | — | — | — |
| Cocoyl amide | 0.5 | 1.0 | 4.0 | 8.0 | 10.0 |
| Preservative | Appropriate amount | Appropriate amount | Appropriate amount | Appropriate amount | Appropriate amount |
| Perfume | Appropriate amount | Appropriate amount | Appropriate amount | Appropriate amount | Appropriate amount |
| Hydrophobically modified polyether polyurethane described in preparation example (A) of the present invention | 1.0 | 1.0 | 1.0 | 1.0 | 1.0 |
| Purified water | to 100 | to 100 | to 100 | to 100 | to 100 |
| Temperature stability (viscosity) | ○ | ◎ | ◎ | ◎ | ○ |
| Visco-elasticity | Δ | ○ | ◎ | ○ | Δ |
| Foam formation | ○ | ◎ | ◎ | ◎ | ○ |
| Foam durability | ○ | ◎ | ◎ | ◎ | ◎ |
| Refreshing sensation | ○ | ◎ | ◎ | ◎ | ○ |
| Viscosity (Pa · s) | | | | | |
| 25° C. $1S^{-1}$ | 0.5 | 0.8 | 8.5 | 15.5 | 34.0 |
| 25° C. $100S^{-1}$ | 0.08 | 0.1 | 0.6 | 0.8 | 1.3 |

The above investigation shows that the best blend ratio of the surfactant in the cleaning agent composition of the present invention is 5–40 wt %.

TABLE 2-6

| | Examples | Comparative example | | |
|---|---|---|---|---|
| | 2-18 | 2-9 | 2-10 | 2-11 |
| Sodium cocoyl methyl taurate | 10.0 | 10.0 | 10.0 | 10.0 |
| Sodium cocoyl glutamate | — | — | — | — |
| Potassium laurate | — | — | — | — |
| Potassium myristate | — | — | — | — |
| Sodium cocoyl isethionate | — | — | — | — |
| Cocoyl amide propyldimethyl glycine | 4.0 | 4.0 | 4.0 | 4.0 |
| Preservative | Appropriate amount | Appropriate amount | Appropriate amount | Appropriate amount |
| Perfume | Appropriate amount | Appropriate amount | Appropriate amount | Appropriate amount |
| Hydrophobically modified polyether polyurethane described in preparation example (A) of the present invention | 1.0 | — | — | — |
| Carboxy vinyl polymer | — | 1.0 | — | — |
| Xanthan gum | — | — | 1.0 | — |
| PEG10000 | — | — | — | 1.0 |
| Purified water | to 100 | to 100 | to 100 | to 100 |

TABLE 2-6-continued

| | Examples | Comparative example | | |
|---|---|---|---|---|
| | 2-18 | 2-9 | 2-10 | 2-11 |
| Temperature stability (viscosity) | ◎ | Δ | Δ | Δ |
| Visco-elasticity | ◎ | ○ | ○ | ○ |
| Foam formation | ◎ | Δ | Δ | ○ |
| Foam durability | ◎ | Δ | Δ | Δ |
| Refreshing sensation | ◎ | Δ | Δ | Δ |
| Viscosity (Pa · s) | | | | |
| 25° C. $1S^{-1}$ | 5.5 | 45.0 | 0.7 | 1.0 |
| 25° C. $100S^{-1}$ | 0.8 | 1.0 | 0.1 | 0.1 |

The above investigation shows that blending hydrophobically modified polyether urethane in the cleaning agent composition of the present invention is significantly superior to blending in other polymer thickeners.

Also, the aforementioned Examples indicate that, in order to obtain high evaluation results for the visco-elasticity (sensory evaluation of the viscosity), the viscosity should preferably be 1–10 Pa·s as measured at 25° C. and $1s^{-1}$ or 0.1–1 Pa·s as measured at 25° C. and $100s^{-1}$.

Other Examples are shown below. Each of these examples is a cleaning agent composition that has superior viscosity and is superior in terms of foam formation as well as foam durability and feels refreshing without a slimy sensation after rinsing-off.

Example 2–19

Body Cleaning Agent

| | |
|---|---|
| Potassium cocoate | 20 |
| Myristyl dimethylaminoacetic acid betaine | 3 |
| Hydrophobically modified polyether polyurethane described in preparation examples A–G of the present invention | 2 |
| Glycerin | 5 |
| Taurine | 2.0 |
| Citric acid | 0.5 |
| Dodecane-1,2-diol acetate sodium salt | 3 |
| Hydroxypropylmethyl cellulose | 0.3 |
| Perfume | Appropriate amount |
| Purified water | Balance (total 100) |

For preparation, the aforementioned ingredients were heated up to 70° C. and dissolved, followed by cooling down to 30° C.

Example 2–20

Gel-like Cleaning Agent

| | |
|---|---|
| Triethanolamine cocoate | 10 |
| Myristyl dimethylaminoacetic acid betaine | 10 |
| Hydrophobically modified polyether polyurethane described in preparation examples A–G of the present invention | 1 |

-continued

| | |
|---|---|
| Glycerin | 5 |
| Citric acid | 0.5 |
| Dodecane-1,2-diol acetate sodium salt | 5 |
| Perfume | Appropriate amount |
| Purified water | Balance (total 100) |

For preparation, the aforementioned ingredients were heated up to 70° C. and dissolved, followed by cooling down to 30° C.

Example 2–21

Shampoo

| | |
|---|---|
| Sodium cocoyl acylmethyl taurate | 10 |
| Cocoyl amide propyldimethyl glycine | 5 |
| Glycerin | 1 |
| Citric acid | 1 |
| Taurine | 1.5 |
| Methyltaurine | 0.5 |
| Hydrophobically modified polyether polyurethane described in preparation examples A–G of the present invention | 0.5 |
| Cationized cellulose | 0.5 |
| Perfume | Appropriate amount |
| Purified water | Balance (total 100) |

For preparation, the aforementioned ingredients were heated up to 80° C. and dissolved, followed by cooling down to 30° C.

Example 2–22

Rinse

| | |
|---|---|
| Sodium N-stearoyl-N-methyl taurate | 2.0 |
| Stearyl alcohol | 8.5 |
| Glycerin | 5.0 |
| Citric acid | 0.03 |
| Hydrophobically modified polyether polyurethane described in preparation examples A–G of the present invention | 0.5 |
| Kathon CG (preservative, from Rohm & Haas) | Appropriate amount |
| Perfume | Appropriate amount |
| Purified water | Balance (total 100) |

Example 2–23

Cleansing Foam

| | |
|---|---|
| Potassium cocoate | 25 |
| Sodium cocoyl N-methyl taurate | 5 |
| Polyethylene glycol 400 | 10 |
| Glycerin | 20 |
| Stearic acid | 3 |
| Dodecane-1,2-diol acetate sodium salt | 3 |
| Taurine | 2 |

-continued

| | |
|---|---|
| Hydrophobically modified polyether polyurethane described in preparation examples A–G of the present invention | 0.5 |
| Perfume | Appropriate amount |
| Purified water | Balance (total 100) |

For preparation, the aforementioned ingredients were heated up to 80° C. and dissolved, followed by cooling down to 30° C.

Example 2–24

Body Shampoo

| | |
|---|---|
| Potassium cocoate | 5 |
| Cocoyl amide propyldimethyl glycine | 2 |
| Propylene glycol | 10 |
| Dodecane-1,2-diol acetate sodium salt | 10 |
| sodium N-cocoyl-N-methyl taurate | 5 |
| Taurine | 1 |
| Hydrophobically modified polyether, polyurethane described in preparation examples A–G of the present invention | 0.5 |
| Perfume | Appropriate amount |
| Purified water | Balance (total 100) |

For preparation, the aforementioned ingredients were heated up to 80° C. and dissolved, followed by cooling down to 30° C.

The following test was conducted to verify the unexpected effect of the present invention.

"Effect of $R^5$ on General Formula (1)"

It was confirmed that the hydrophobic association of the associative thickener of general formula (1) is enhanced by lengthening of the chain of the end hydrophobic group and the system can be thickened more effectively.

A cone/plate type or concentric cylinder type viscometer was used for the viscosity mearurement, and the apparent viscosity at 25° C. and $1s^{-1}$, and $100s^{-1}$, was determined.

TABLE 2-7

| $R^5$ Number of carbon atoms[*1] | Viscosity of 1% simple aqueous solution (Pa · s) | | Viscosity of shampoo[*2] (Pa · s) | |
|---|---|---|---|---|
| | 25° C. $1S^{-1}$ | 25° C. $100S^{-1}$ | 25° C. $1S^{-1}$ | 25° C. $100S^{-1}$ |
| 12 | 0.06 | 0.04 | 0.2 | 0.04 |
| 16 | 0.40 | 0.12 | 1.9 | 0.1 |
| 18 | 1.2 | 0.15 | 3.4 | 0.2 |
| 24 | 3.8 | 0.18 | 9.0 | 0.4 |

[*1]Associative thickeners (hydrophobically modified polyether urethane) with different numbers of carbons in $R^5$ were prepared in a similar manner as in Preparation example A.

The compound having 24 carbon atoms is the hydrophobically modified polyether urethane of Preparation example A.

The compound having 18 carbon atoms was prepared by using EO 20-mole adduct of stearyl alcohol for the compound corresponding to general formula (10) of Preparation example A.

The compound having 16 carbon atoms was prepared by using EO 20-mole adduct of cetyl alcohol for the compound corresponding to general formula (10) of Preparation example A.

The compound having 16 carbon atoms was prepared by using EO 20-mole adduct of lauryl alcohol for the compound corresponding to general formula (10) of Preparation example A.

| *2: Shampoo recipe | |
|---|---|
| Sodium cocoyl methyl taurate | 10 wt % |
| Cocoyl amide propyldimethyl glycine | 6 wt % |
| Associative thickener shown in the table | 0.5 wt % |
| Cationized starch | 0.5 wt % |
| Ion-exchange water | Balance |

The aforementioned investigation shows that the thickening effect is enhanced not only in the simple aqueous solution but also in the hair treatment agent composition of the present invention when hydrophobically modified polyether urethane whose $R^5$ has 24 carbon atoms is used.

"The effect of the cationized starch"

A shampoo was prepared with the following recipe and the smooth sensation and sticky sensation during rinsing after using the shampoo were evaluated.

The testing was conducted using the shampoo prepared with the following recipe.

| | |
|---|---|
| Sodium cocoyl N-methyl taurate | 10 wt % |
| Cocoyl amide propyldimethyl glycine | 6 wt % |
| Compound of preparation example A of the present invention | 0.5 wt % |
| Cationized starch or catinonized cellulose | Amount indicated below |
| Ion-exchange water | Balance |

Evaluattion Method

Evaluation used an absolute scale of seven steps (−3, −2, −1, 0, +1, +2, and +3).

−3 and +3 were evaluated as follows.

Smooth sensation; (not smooth at all: −3→very smooth: +3)

Sticky sensation; (very sticky: −3→not sticky at all: +3)

The average of a panel of 8 persons was determined and the judgment was made based on the following:

x: Below −1.5
Δ: −1.5 to below +0.5
○: +0.5 to below +1.5
◎: +1.5 or above

TABLE 2-8

| Blend ratio (wt %) | Smooth sensation during rinsing | Lack of stickiness |
|---|---|---|
| Cationized starch | | |
| 0 | x | ◎ |
| 0 1 | Δ | ◎ |
| 0 2 | ○ | ◎ |
| 0 5 | ○ | ◎ |
| 1 0 | ◎ | ◎ |
| 1 5 | ◎ | ◎ |
| Cationaized cellulose | | |
| 0 5 | ○ | Δ |
| 1 0 | ◎ | x |

The above results show that use of a shampoo containing cationized starch results in smooth rinsing and gives good sensation without stickiness during use.

Other Examples of the present invention are shown below. In all of the following Examples, the hydrophobically modified polyether urethane is a commercial product (Adecanol GT-700 from Asahi Denka Kogyo).

Example 2–25

Shampoo

| | Wt % |
|---|---|
| Purified water | Balance to make the total of 100 weight parts |
| Cationaized cellulose (JR −400 from Union Carbide Corporation) | 0.50 |
| Sodium N-cocoyl-N-methyl taurate | 5.00 |
| Ethylene glycol distearate | 2.00 |
| Cocoyl monoethanol amide | 0.60 |
| Citric acid | Amount neede to adjust pH to 5.3 |
| Propylene glycol laurate | 2.00 |
| Hydrophobically modified polyether polyurethane | 0.50 |
| Sodium benzoate | 0.30 |
| Disodium edetate | 0.01 |
| Phenoxyethanol | 0.20 |
| Blended perfume | 0.60 |
| Cocoyl amide propyldimethyl glycine | 4.00 |
| Lauryl dimethylamino acetic acid betaine | 4.00 |

Cationized cellulose was hydrated with purified water at normal temperatures and, after raising the temperature up to 80° C., other ingredients were added; after stirring and mixing, the temperature was lowered to obtain a shampoo.

Example 2–26

Shampoo

| | Wt % |
|---|---|
| Purified water | Balance to make the total of 100 weight parts |
| Cationic polymer (Merquat 550 from Nalco Chemical Company) | 0.50 |
| Polyoxyethylene (2) sodium lauryl ether sulfate | 9.00 |
| Dipropylene glycol | 3.00 |
| Ethylene glycol distearate | 2.00 |
| Cocoyl monoethanol amide | 2.50 |
| Hydrophobically modified polyether polyurethane | 0.50 |
| POP-POE block copolymer (Pluaronic L-64 from Asahi Denka Kogyo) | 0.50 |
| Preservative (Kathon CG) | 0.05 |
| Disodium edetate | 0.01 |
| Blended perfume | 0.60 |
| L-glutamic acid | Amount neede to adjust pH to 5.0 |
| Cocoyl amide propyldimethyl glycine | 7.00 |
| Silicon emulsion (BY22-005 from Dow Corning Toray Co., Ltd.) | 1.00 |

The ingredients were added one after another to purified water and stirred and mixed at 80° C., followed by cooling to obtain a shampoo.

Example 2–27

Shampoo

| | Wt % |
|---|---|
| Purified water | Balance to make the total of 100 weight parts |
| Cationized starch | 0.20 |
| Polyoxyethylene (2) sodium lauryl ether sulfate | 12.00 |
| Propylene glycol | 5.00 |
| Cocoyl monoethanol amide | 2.00 |
| Hydrophobically modified polyether polyurethane | 0.50 |
| Preservative (Kathon CG) | 0.05 |
| Disodium edetate | 0.01 |
| Blended perfume | 0.60 |
| Succinic acid | Amount neede to adjust pH to 5.0 |
| Cocoyl amide propyldimethyl glycine | 7.00 |

The ingredients were added one after another to purified water and stirred and mixed at 80° C., followed by cooling to obtain a shampoo.

Example 2–28

Shampoo

| | Wt % |
|---|---|
| Purified water | Balance to make the total of 100 weight parts |
| Cationaized cellulose (Catinal LC-100 from Toho Chemical Industry Co., Ltd.) | 0.30 |
| Polyoxyethylene (2) sodium lauryl ether sulfate | 18.00 |
| Decaglycerin monooleate | 1.00 |
| Cocoyl monoethanol amide | 2.00 |
| Hydrophobically modified polyether polyurethane | 0.50 |
| Preservative (Kathon CG) | 0.05 |
| Disodium edetate | 0.01 |
| Blended perfume | 0.60 |
| Lactic acid | Amount neede to adjust pH to 5.0 |
| Dipotassium glycyrrhizate | 0.10 |
| Taurine | 2.00 |
| Sodium pyrrolidone carboxylate | 0.10 |
| Cocoyl amide propyldimethyl glycine | 5.00 |

The ingredients were added one after another to purified water and stirred and mixed at 80° C., followed by cooling to obtain a shampoo.

Example 2–29

Hair Manicure Conditioner

| | Wt % |
|---|---|
| Purified water (1) | 20.00 |
| Dimethyl polysiloxane gum: imethyl polysiloxane 20 m Pa · s (20:80) | 1.00 |
| Cetostearyl alcohol | 9.00 |
| Sodium N-stearoyl-N-methyl taurate | 1.00 |
| Benzyl alcohol | 5.00 |
| Glycerin monooleate | 1.00 |
| Hydrophobically modified polyether polyurethane | 0.50 |
| Royal jelly extract | 0.05 |
| Disodium edetate | 0.01 |
| Blended perfume | 0.60 |
| Citric acid | Amount neede to adjust pH to 3.0 |
| Alizurol purple | 0.08 |
| Taurine | 2.00 |
| Purified water | Balance to make the total of 100 weight parts |

The ingredients were added one after another to 20 parts of purified water and stirred and mixed at 80° C., followed by cooling; the rest of the purified water at normal temperature was then added and the temperature was lowered by means of a heat exchanger to obtain a hair manicure conditioner (cleaning agent rinse).

Example 2–30

Shampoo

| | Wt % |
|---|---|
| Purified water | Balance to make the total of 100 weight parts |
| Cationaized cellulose (JR-400 from Union Carbide Corporation) | 0.50 |
| Sodium N-cocoyl-N-methyl taurate | 5.00 |
| Ethylene glycol distearate | 2.00 |
| Cocoyl monoethanol amide | 0.60 |
| Citric acid | Amount neede to adjust pH to 5.3 |
| Propylene glycol laurate | 2.00 |
| Hydrophobically modified polyether polyurethane | 0.50 |
| Sodium benzoate | 0.30 |
| Disodium edetate | 0.01 |
| Phenoxyethanol | 0.20 |
| Blended perfume | 0.60 |
| Cocoyl amide propyldimethyl glycine | 4.00 |
| Lauryl dimethylamino acetic acid betaine | 4.00 |

Cationized cellulose was hydrated with purified water at normal temperatures and, after raising the temperature up to 80° C., other ingredients were added; after stirring and mixing, the temperature was lowered to obtain a shampoo.

Example 2–31

Shampoo

| | Wt % |
|---|---|
| Purified water | Balance to make the total of 100 weight parts |
| Cationic polymer (Merquat 550 from Nalco Chemical Company) | 0.50 |
| Polyoxyethylene (2) sodium lauryl ether sulfate | 9.00 |

-continued

| | Wt % |
|---|---|
| Dipropylene glycol | 3.00 |
| Ethylene glycol distearate | 2.00 |
| Cocoyl monoethanol amide | 2.50 |
| Hydrophobically modified polyether polyurethane | 0.50 |
| POP-POE block copolymer (Pluaronic L-64 from Asahi Denka Kogyo) | 0.50 |
| Preservative (Kathon CG) | 0.05 |
| Disodium edetate | 0.01 |
| Blended perfume | 0.60 |
| L-glutamic acid | Amount neede to adjust pH to 5.0 |
| Cocoyl amide propyldimethyl glycine | 7.00 |
| Silicon emulsion (BY22-005 from Dow Corning Toray Co., Ltd.) | 1.00 |

The ingredients were added one after another to purified water and stirred and mixed at 80° C., followed by cooling to obtain a shampoo.

Example 2–32

Shampoo

| | Wt % |
|---|---|
| Purified water | Balance to make the total of 100 weight parts |
| Cationized starch | 0.20 |
| Polyoxyethylene (2) sodium lauryl ether sulfate | 12.00 |
| Propylene glycol | 5.00 |
| Cocoyl monoethanol amide | 2.00 |
| Hydrophobically modified polyether polyurethane | 0.50 |
| Preservative (Kathon CG) | 0.05 |
| Disodium edetate | 0.01 |
| Blended perfume | 0.60 |
| Succinic acid | Amount neede to adjust pH to 5.0 |
| Cocoyl amide propyldimethyl glycine | 7.00 |

The ingredients were added one after another to purified water and stirred and mixed at 80° C., followed by cooling to obtain a shampoo.

Example 2–33 shampoo

| | Wt % |
|---|---|
| Purified water | Balance to make the total of 100 weight parts |
| Cationaized cellulose (Catinal LC-100 from Toho Chemical Industry Co., Ltd. ) | 0.30 |
| Polyoxyethylene (2) sodium lauryl ether sulfate | 18.00 |
| Monoolein acid deca glycerin | 1.00 |
| Cocoyl monoethanol amide | 2.00 |
| Hydrophobically modified polyether polyurethane | 0.50 |
| Preservative (Kathon CG) | 0.05 |
| Disodium edetate | 0.01 |
| Blended perfume | 0.60 |
| Lactic acid | Amount neede to adjust pH to 5.0 |

-continued

| | Wt % |
|---|---|
| Dipotassium glycyrrhizate | 0.10 |
| Taurine | 2.00 |
| Sodium pyrrolidone carboxylate | 0.10 |
| Cocoyl amide propyldimethyl glycine | 5.00 |

The ingredients were added one after another to purified water and stirred and mixed at 80° C., followed by cooling to obtain a shampoo.

Industrial Applicability

The present invention provides a hair treatment agent composition which has good temperature stability in terms of the viscosity, exhibits superior fluid flow characteristics, achieves smoothness and ease of arranging the hair after drying, and gives a superior sensation during use.

The present invention can provide a cleaning agent composition that has superior viscosity and is superior in terms of foam formation as well as foam durability and feels refreshing without a slimy sensation after rinsing-off.

The invention claimed is:

1. A hair treatment composition comprising the following ingredients A, B, C and D:

(A) a hydrophobically modified polyether urethane represented by the following general formula (1):

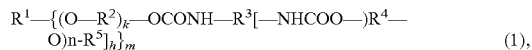

wherein $R^1$, $R^2$, and $R^4$ denote hydrocarbon groups which can be identical or different from each other, $R^1$ is a residue of a polyol represented by $R^1$—$(OH)_m$, $R^2$ and/or $R^4$ are alkylene groups having 2–4 carbon atoms or phenylethylene groups that can be identical or different from each other, $R^3$ denotes a hydrocarbon group that can have a urethane bond, or a residue of a polyisocyanate represented by $R^3$—$(NCO)_{h+1}$, which is obtained by a reaction between di- to octa-hydric polyol and di- to tetra-hydric polyisocyanate, $R^5$ is a hydrocarbon group having 24 carbon atoms derived from decyltetradecyl alcohol; m is 2 or greater; h is 1 or greater; and k and n are independent numbers in the range of 0–1,000, or the polyether urethane of formula 1 is a product of a reaction between one, two or more polyether polyols represented by $R^1$—$(NCO)_{h+1}$, and one, two or more polyether monoalcohols represented by HO—$(R^4$—$O)_n$—$R^5$;

(B) a cationic surfactant, which is a quaternary ammonium salt represented by the following general formula (2) or an amidoamine type compound represented by the following general formula 3:

wherein, in general formula 2, R3 denotes an alkyl group or hydroxyalkyl group having 14–22 carbon atoms, R4 denotes a benzyl group, hydroxyalkyl group, or alkyl group having 1–3 carbon atoms, R5 and R6 denote alkyl groups or hydroxyalkyl groups independently represented by either R3 or R4, and X denotes a halogen atom or an alkylsulfuric group having 1–2 carbon atoms and, $$R7CONH—(CH_2)_xN(R8)_2 \quad 3$$

wherein R7CO— denotes a higher fatty acid residue having 12–24 carbon atoms, R8 denotes an alkyl group having 1–4 carbon atoms, and x is an integer 2–4, or the amidoamine-type compound is one, two or more selected from a group consisting of stearamidoethyl diethylamine, stearamidopropyl dimethylamine, and behenamidopropyl dimethylamine, or one, two or more quaternary ammonium salts selected from the group consisting of stearylmethyl ammonium chloride, cetylmethyl ammonium chloride, and behenyltrimethyl ammonium chloride;

(C) a higher alcohol and/or higher fatty acid, wherein the molar ratio of the surfactant and the higher alcohol and/or higher fatty acid is 1:2–1:10, the higher alcohol is one, two or more selected from the group consisting of cetyl alcohol, stearyl alcohol, and behenyl alcohol, said higher fatty acid is one, two or more selected from the group consisting of stearic acid, palmitic acid, myristic acid, oleic acid, isostearic acid, 12-hydroxystearic acid, and behenic acid, and the blend ratio of the hydrophobically modified polyether urethane of general formula (1) is 0.1–10 wt % of the total amount of the hair treatment composition; and (D) an organic acid selected from the group consisting of citric acid, tartaric acid and glutamic acid.

2. The hair treatment composition of claim 1, wherein the viscosity of the hair treatment agent composition is 1–10 PaAs when measured at 25EC and 1s$^{-1}$ and/or 0.1–1 PaAs when measured at 25EC and 100s$^{-1}$.

3. The hair treatment agent composition of claim 1, wherein said hair treatment composition is a hair conditioning agent.

4. The hair treatment composition of claim 1, wherein said organic acid is tartaric acid or glutamic acid.

5. A cleaning composition comprising the following ingredients (A),(B) and (C):

(A) a hydrophobically modified polyether urethane represented by the following general formula 1:

General Formula 1

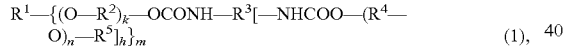

$$R^1—\{(O—R^2)_k—OCONH—R^3[—NHCOO—(R^4—O)_n—R^5]_h\}_m \quad (1),$$

wherein R$^1$, R$^2$, and R$^4$ denote hydrocarbon groups which can be identical or different from each other, R$^1$ is a residue of a polyol represented by R$^1$—(OH)$_m$, R$^2$ and/or R$^4$ are alkylene groups having 2–4 carbon atoms or phenylethylene groups that can be identical or different from each other, R$^3$ denotes a hydrocarbon group that can have a urethane bond, or a residue of a polyisocyanate represented by R$^3$—(NCO)$_{h+1}$, R$^5$ is a hydrocarbon group having 24 carbon atoms derived from decyltetradecyl alcohol; m is 2 or greater; h is 1 or greater; and k and n are independent numbers in the range of 0–1,000, or the hydrophobically modified polyether urethane represented by general formula 1 is a product of a reaction between one, two or more polyether polyols represented by R$^1$—((O—R$^2$)$_k$—OH))$_m$, one, two or more residues of polyisocyanates represented by R$^3$—(NCO)$_{h+1}$, and one, two or more polyether monoalcohols represented by HO—(R$^4$—O)$_n$—R$^5$, (B) an anionic surfactant and/or ampholytic surfactant and/or ampholytic surfactant, wherein the anionic surfactant is represented by the following general formulas 4, 5 or 5, General Formula 4

$$R1CO—A—(CH_2)_nSO_3M1 \quad (4)$$

wherein R1CO— denotes a saturated or unsaturated fatty acid residue having 10–22 carbon atoms on average, A denotes any of the structures containing electron donor atoms —O—, —NH—, and/or —N(CH$_3$)—, M1 denotes hydrogen, alkali metal, alkaline earth metal, ammonium or organic amine, and n denotes an integer 1–3;

General Formula 5

$$R2CONH—C(b)H—COOM2 \quad (5)$$

wherein R2CO— denotes a saturated or unsaturated fatty acid residue having 10–22 carbon atoms on average, b denotes a hydrogen atom, —CH$_3$, or —(CH$_2$)n-COOM3, M2 and M3 denote hydrogen, alkali metal, alkaline earth metal, ammonium or organic amine, and n denotes an integer 1–3; and General Formula (6):

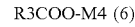

$$R3COO-M4 \quad (6)$$

wherein R3COO— denotes a saturated or unsaturated fatty acid residue having 10–22 carbon atoms on average, M4 denotes hydrogen, alkali metal, alkaline earth metal, ammonium or organic amine and n denotes an integer 1–3, the anionic surfactant is one, two or more chosen from a group consisting of N-acylmethyl taurate, N-acyl taurate, and N-acyl isethionate, the ampholytic surfactant is an acetic acid betaine type or imidazoline type ampholytic surfactant, the weight ratio between the anionic surfactant and the ampholytic surfactant is 10:0–2:8, the blend ratio of the hydrophobically modified polyether urethane of general formula 1 is 0.1–10 wt % of the total amount of the cleaning agent composition, the blend ratio of the anionic surfactant or the ampholytic surfactant is 5–40 wt % of the total amount of the cleaning composition; and (C) 0.2–1.5 wt % cationized starch.

6. The cleaning agent composition of claim 5, wherein the viscosity of the cleaning agent composition is 1–10 PaAs when measured at 25EC and 1s$^{-1}$ and/or 0.1–1 PaAs when measured at 25EC and 100s$^{-1}$.

* * * * *